United States Patent
Sufka

(10) Patent No.: US 8,999,293 B2
(45) Date of Patent: Apr. 7, 2015

(54) ANIMAL MODEL OF ANXIETY AND DEPRESSION

(71) Applicant: Kenneth J. Sufka, Oxford, MS (US)

(72) Inventor: Kenneth J. Sufka, Oxford, MS (US)

(73) Assignee: University of Mississippi, University, MS (US)

( * ) Notice: Subject to any disclaimer, the term of this patent is extended or adjusted under 35 U.S.C. 154(b) by 0 days.

(21) Appl. No.: 13/895,107

(22) Filed: May 15, 2013

(65) Prior Publication Data
US 2013/0287694 A1      Oct. 31, 2013

Related U.S. Application Data

(63) Continuation-in-part of application No. 11/549,322, filed on Oct. 13, 2006.

(60) Provisional application No. 61/726,121, filed on Oct. 13, 2005.

(51) Int. Cl.
| | |
|---|---|
| *A61K 49/00* | (2006.01) |
| *A01H 5/00* | (2006.01) |
| *A61B 5/16* | (2006.01) |
| *A01K 45/00* | (2006.01) |
| *A01K 67/02* | (2006.01) |

(52) U.S. Cl.
CPC .............. *A61K 49/0008* (2013.01); *A61B 5/16* (2013.01); *A01K 45/00* (2013.01); *A01K 67/02* (2013.01); *A01K 2227/30* (2013.01); *A01K 2267/0356* (2013.01)

(58) Field of Classification Search
CPC  A61K 49/00; A61K 49/0004; A61K 49/0008
See application file for complete search history.

(56) References Cited

U.S. PATENT DOCUMENTS

| | | | |
|---|---|---|---|
| 5,106,616 A | 4/1992 | McAnalley et al. | |
| 5,773,425 A | 6/1998 | McAnalley et al. | |
| 2003/0215531 A1 | 11/2003 | Stogniew et al. | |

OTHER PUBLICATIONS

Rogers, L.J., et al., "Separate Chemical Inhibitors of Long-Term and Short-Term Memory: Contrasting Effects of Cycloheximide, Ouabain and Ethacrynic Acid on Various Learning Tasks in Chickens", 1977, Pro. Royal. Soc. B, pp. 171-195.*
Freire, R., et al., "Pre- and post-hatching effects of corticosterone treatment on behavior of the domestic chick", 2006, Hormones and Behavior, pp. 157-165.*
Osborne, NN., et al., "Tricyclic antidepressants, mianserin, and ouabain stimulate inositol phosphate formation in vitro in rat cortical slices", Neurochem Res., 1988, Abstract, pp. 1-2.*
Coop de Ville, "Welcome to "Coop de Ville" . . . ain't nobody here but us chickens!", accessed from:http://www.jfolse.com/On%20the%20Farm%20WOP/Coop%20de%20Ville.html, accessed on Jul. 9, 2014, pp. 1-7.*
Flock, D.K. "Lohrman Information, A history of layer breeding in Cuxhaven since 1959: from serendipity to sustainability", 2009, pp. 1-7.*
Avula, Bharathi, et al., High-Performance Liquid Chromatogiaphic Determination of Xanthohumol in Rat Plasma, Urine, and Fecal Samples, Journal of Chromatographic Science, vol. 42, Aug. 2004.
Baldauf, K., Opiate Modulation of Monoamines in the Chick Forebrain: Possible Role in Emotional Regulation? Journal of Neurobiol Feb. 5, 2005, 62(2) 149-163.
Baldessarini, Ross J., Drugs and the Treatment of Psychiatric Disorders, Depression and Anxiety Disorders Drugs Acting on the Central System. Chapter 19, Section III.
Beasley, Charles M. Jr., M. D. et al., Fluoxetine Compared with Imipramine in the Treatment of Inpatient Depression—A multicenter Trial Annals of Clinical Psychiatry 6 199-208,1993, 1993 Elsevier Science Publishing Co. Inc.
Coleman, Dr. Paul D., Neurobiology of Aging—Research on Age-Related Phenomena, Neurodegeneration and Neuropathology, Pergamon Press.
Cook, Christian J., Stress Induces DRF Release in the Paraventricular Nucleus, and Both CRF and GABA Release in the Amygdala Physiology and Behavior 82 (2004) 751-762.
de Jonghe, F. et al., A Randomized, Double-Blind Study of Fluoxetine and Maprotiline in the Treatment of Major Depression Pharmacopsychiat, 24 (1991) 62-67.
Dunn, Adrian J., et al., Cytokines as Mediators of Depression: What can we learn from animal studies? Neuroscience and Biobehavioral Reviews 29 (2005) 891-909.
Feltenstein, Matthew W. et al., Anti-inflammatory and Anti-hyperalgesc Effects of Sesquiterpene Lactones from Magnolia and Bear's Foot Pharmacology Biochemistry and Behavior 79 (2004) 299-302.
Feltenstein, Matt W., et al., Anxiolytic Properties of Piper Methysticum Extract Samples and Fractions in the Chick Social-Separation-Stress Procuedure, Phytotherapy Research, Phytother Res. 17, 210-216 (2003)m, Wiley InterScience DOI 10 1002/ptr. 1107.
Feltenstein. Matthew W. et al., Screening Antidepressants in The Chick Separation-Stress Paradigm, Psychopharmacology (2005) 181 153-159.
Feltenstein, Matthew W. et al., Corticosterone Response in the Chick Separation-Stress Paradigm, Physiology & Behavior 78 (2003) 489493.
Feltenstein. Matthew W. et al., Dissociation of Stress Behaviors in the Chick, Physiology & Behavior 75 (2002) 675-579.

(Continued)

*Primary Examiner* — Michael G Hartley
*Assistant Examiner* — Lance Rider
(74) *Attorney, Agent, or Firm* — Butler Snow LLP

(57) ABSTRACT

This invention relates generally to animal models of anxiety and depression. Specifically, this invention relates to an in vivo high utility, high-throughput model for screening anxiolytic/antidepressant drugs in fowl chicks with stress vulnerability. This new animal model utilizes an inexpensive avian model, measures spontaneous behaviors in very young animals, and is capable of detecting and/or differentiating a compound's anxiolytic and/or antidepressant effects. This new animal model is especially useful in detecting and/or differentiating a compound's anxiolytic and/or antidepressant effects in treatment-resistant subjects. Animal costs are less than 10% of rodent costs and the assay can be run in a high-throughput mode.

6 Claims, 19 Drawing Sheets

(56) References Cited

OTHER PUBLICATIONS

Feltenstein, Matt W. et al., The Chick Separation Stress Paradigm: A Validation Study, Pharmacology Biochemistry and Behavior 77 (2003) 221-226.
Fuller, Ray W. et al., Inhibition of Serotonin Reuptake, Federation Proceedings vol. 36, No. 8—Jul. 1977.
Gallup, Gordon G. Jr., et al., An Ethological Analysis of Open-Ended Behaviour in Chickens, Anim. Behav. 1980, 28, 368-378.
Gorman, Jack M. MD et al., An Open Trial of Fluoxetine in the Treatment of Panic Attacks, J Clin Psychopharmacol, vol. 7., No. 5, Oct. 1987.
Hughes, Richard A. et al., Morphine Hyperalgesic Effects on Developmental Changes in Thermal Nociception and Respiration in Domestic Fowl, Pharmacology Biochemistry and Behavior, vol. 42. pp. 535-539, 1992.
Hughes, Richard A. et al., Morphine Hyperalgesic Effects on the Formalin Test in Domestic Fowl, Pharmacology Biochemistry and Behavior vol. 38, pp. 247-251 Pergamon Press plc 1991.
Hughes, Richard A. et al., The Ontogeny of Thermal Nociception in Domestic Fowl Thermal Stimulus Intensity and Isolation Effects, Developmental Psychobiology vol. 23, Issue 2, pp. 129-140.
Kessler. Ronald C., PhD, et al., Lifetime and 12-Month Prevalence of OSM-III-R Psychiatric Disorders in the United States, Arch Gen Psychiatry, vol. 51, Jan. 1994.
Kessler Ronald C. PhD et al., Lifetime Prevalence and Age-of-Onset Distributions of DSM-IV Disorders in the National Comorbidity Survey Replication, Arch Gen Psychtalry, vol. 62, Jun. 2005.
Lehr, E, Distress Call Reactivation in Isolated Chicks A behavioral Indicator With High Selectivity for Antidepressants, Psychopharmacology (1989) 97 145-156, Spnnger-Verlag 1989.
Long, Scott F. et al., The Effects of Cocaine and Nandrolone Co-Administration on Aggression in Male Rats, Prog Neuro-Psychopharmacol & Biol Psychiat 1996 vol. 20 pp. 839-856.
McCurdy, Christopher R. et al., Antinociceptive Profile of Salvinorin A, a Structurally Unique Kappa Opioid Receptor Agonist, Pharmacology Biochemistry and Behavior 83 (2006) 109-113.
Michelson, David et al., Continuing Treatment of Panic Disorder After Acute Response Randomised, Placebo-Controlled Trial with Fluoxetine, British Journal of Psychiatry (1999) 174 213-218.
Michelson, David et al., Outcome Assessment and Clinical Improvement in Panic Disorder Evidence from a Randomized Controlled Trial of Fluoxetine and Placebo, Am J Psychiatry 155 Nov. 11, 1998.
Mormede, Cecile et al., Chronic Mild Stress in Mice Decreases Peripheral Cytokine and Increases Central Cytokine Expression Independently of IL-10 Regulation of the Cytokine Network, NeuroImmunoModulation Mar. 2002, 10 359-386.
Nestler, Eric J et al., Antidepressant Treatments in the 21st Century, 1998 Society of Biological Psychiatry 44 526-533.
Nielsen, B.M. et al., A comparison of Fluoxetine and Imipramine in the Treatment of Outpatients with Major Depressive Disorder, ACTA Psychiatrica Scandinavica 1993 87: 269-272 printed in Belgium.
Northoff, H. et al., Immunologic Mediators as Parameters of the Reaction to Strenuous Exercise, Int J Sports Med 12 (1991).
Pike, Jennifer L. et al., Dissociation of Inflammatory Markers and Natural Killer Cell Activity in Major Depressive Disorder, Brain, Behavior, and Immunity 20 (2006)169-174.
Plotsky, Paul M. et al., Central and Feedback Regulation of Hypothalamic Corticotropin-Releasing Factor Secretion, Ciba Foundation Symposium 1993, 172 59-75 discussion 75-84.
Roach, J. Todd et al., Characterization of the Chick Carrageenan Response, Brain Research 994 (2003) 216-225.
Sapolsky, Robert M. et al., Glucocorticoid Feedback Inhibition of Adrenocorticotropic Hormone Secretagogue Release, Neuroendocrinology 1990 51 328-336.
Scavone, Joseph M. et al., Alprazolam Kinetics Following Sublingual and Oral Administration, J Clin Psychopharmacol, vol. 7, No. 5., Oct. 1987.
Smith, Kenyatta K., et al., Anxiolytic Effects of Kava Extract and Kavalactones in the Chick Social Separation-Stress Paradigm, Psychopharmacology (2001) 155 86-90.
Sufka, Kenneth J., et al., Analgesic Effects of S and R Isomers of the Novel 5-HT3 Receptor Antagonists ADR-851 and ADR-882 in Rats, European Journal of Pharmacology 204 (1991) 117-119.
Sufka, Kenneth J., et al., Anxiolytic Properties of Botanical Extracts in the Chick Social Separation-Stress Procedure, Psychopharmacology (2001)153 219-224.
Sufka, Kenneth J., Central & Peripheral Nervous System, Novel Approaches for Analgesic Drug Assessment New Animal Paradigms, Exp Opin Invest Drugs (1996) 5(4) 421-428.
Sufka, Kenneth J. et al., Central Monoaminergic Changes Induced by Morphine in Hypoalgeslc and Hyperalgesic Strains of Domestic Fowl, Pharmacology Biochemistry and Behavior vol. 42, pp. 781-785, 1992.
Sufka, Kenneth J., Conditioned Place Preference Paradigm: A Novel Approach for Analgesic Drug Assessment Against Chronic Pain, Pain 58 (1994) 355-366.
Sufka, Kenneth J. et al., Construct Validation of Behavioral Indices of Isolation Stress and Inflammatory Nociception in Young Domestic Fowl, Physiology & Behavior, vol. 55. No. 4, pp. 741-746, 1994.
Sufka, Kenneth J., et al., Differential Effects of Handling on Isolation-Induced Vocalizations, Hypoalgesia, and Hyperthermia in Domestic Fowl, Physiology & Behavior, vol. 50, pp. 129-133 Pergamon Press plc 1991.
Sufka, Kenneth J., et al., Dose and Temporal Parameters of Morphine-Induced Hyperalgesia in Domestic Fowl, Physiology & Behavior, vol. 47 pp. 335-337, Pegamon Press plc 1990.
Sufka, Kenneth J. et al., Effects of Calcitonin on CNS Monoamines Following Carrageenan-Induced Inflammation in Rats, Pharmacology Biochemistry and Behavior, vol. 45, pp. 507-511, 1993.
Sufka, Kenneth J., et al., Effects of Selective Opiate Antagonists on Morphine-Induced Hyperalgesia in Domestic Fowl, Pharmacology Biochemistry & Behavior, vol. 38, pp. 49-54, Pergamon Press plc, 1991.
Sufka, Kenneth J., et al., Functional Deficits Following Bilateral Forelimb Adjuvant Inflammation Assessed by Operant Methodology Effects of Indomethacin and Morphine on Recovery of Function, Expermental & Clinical Psychopharmacology, 1996 vol. 4 No. 3, 336-343.
Sufka, Kenneth J., et al., Opiate Effects on Isolation Stress in Domestic,Fowl, Pharmacology Biochemistry & Behavior, vol. 49. No. 4, pp. 1011-1015, 1994.
Sufka, Kenneth J., et al., Receptor Mediation of 5-HT-Induced Inflammation and Nociception in Rats, Pharmacology Biochemistry & Behavior, vol. 41, pp. 53-56, Pergamon Press plc, 1991.
Willner, Paul, Validity, Reliability and Utility of the Chronic Mild Stress Model of Deptession a 10-Year Review and Evaluation, Psychopharmacoloay (1997) 134 319-329.
Wittchen, Hans-Ulrich PhD et al. DSM-III-R Generalized Anxiety Disorder in the National Comorbidity Survey, Arch Gen Psychiatry vol. 51 May 1994.
Zhou, Daohong et al. Exposure to Physical and Psychological Stressors Elevates Plasma Interleukm 6, Endocrinology vol. 133, 1993.
Weinstock, M. et al., "Effect of TV3326, a novel mooamine-oxidase . . . ", 2002, Psychopharmacology, 160, pp. 318-324.
Panksepp, J., at al., "Effects of ACTH(1-24) and ACTH/MSH(4-10) . . . ", 1990, Peptides, 11, pp. 915-919.
Sufka; Kenneth J., et al., Scoring the Mouse Formalin Test Validation Study, European Journal of Pain (1998) 2, 351-358.
Sufka, Kenneth J. et al., Stimulus Properties and Artinociceptive Effects of Selective Bradyknin B1 and B2 Receptor Antagonists in Rats, Pain, 66 (1996) 99-103.
Sufka, Kenneth J. et al., Time-Dependent Codeine Hypoalgesia and Hyperalgesia in Domestic Fowl, Pharmacology Biochemistiy & Behavior. vol. 41 pp. 349-353,1992.
Uhlenhuth, E. H. M.D. et al., Do Antidepressants Selectively Suppress Spontaneous (Unexpected) Panic Atlacks a Replication, Journal of Clinical Psychopharmacology, V. 20 N. 6.
Warnick, Jason E. et al., Opiod Receptor Function in Social Attachment in Young Domeslic Fowl, Behavioural Brain Research 160 (2005) 227-285.
Watson, G. Stennis et al., Benzodiazepine Receptor Function in the Chick Social Separation-Stress Procedure, Experimental and Clinical Psychopharmacology 1999 V 7 N 2 83-89.

(56) References Cited

OTHER PUBLICATIONS

Watson, G. Stennis et al., Experimental and Clinical Psychopharmacology, 1996, vol. 4, No. 4, 347-353.
Watson, G. Stennis et al., Optimal Scoring Strategies and Weights for the Formalin Test in Rats, Pain 70 (1997) 53-58.
Wells, Barbara G., Pharm D et al., Pharmacotherapy vol. 1 No. 2 Sep./Oct. 1981.
Willner, Paul V.;Behavioral Models in Psychopharmacology—Introductron, Behavioural Models in Psychopharmacology Theoretical Industrial and Clinical Procedures, Part 1 pp. 3-18.

* cited by examiner

ANIMAL MODEL OF ANXIETY AND DEPRESSION

CROSS-REFERENCES TO RELATED APPLICATIONS

This application is a continuation in part of U.S. patent application Ser. No. 11/549,322, filed Oct. 13, 2006, which claims priority to U.S. Provisional Application Ser. No. 60/726,121 filed Oct. 13, 2005 (the entire contents of which are hereby specifically incorporated by reference in its entirety) under 35 U.S.C. §119(e).

FIELD OF THE INVENTION

This invention relates generally to animal models of anxiety and depression. Specifically, this invention relates to an in vivo high utility, high-throughput model for screening anxiolytic/antidepressant drugs in fowl chicks with stress vulnerability and/or treatment-resistance.

BACKGROUND OF THE INVENTION

Recent U.S. Mental Health Surveys report alarmingly high lifetime prevalence rates of 20.8% and 28.8% for mood disorders and anxiety disorders, respectively (R. C. Kessler et al. *Lifetime Prevalence And Age-Of-Onset Distributions Of DSM-IV Disorders In The National Comorbidity Survey Replication*, 62 Arch. Gen. Psychiatry 593-02 (2005)). While most who suffer from these clinical syndromes indeed seek treatment help, antidepressant therapies that target monoaminergic (MA) systems are problematic as they require 4-6 weeks of administration to achieve effects, are accompanied by unpleasant side effects, possess modest efficacy rates (65%), and display significant relapse rates (M. E. Thase. *Handbook of Depression*, I. H. Gotlib & C. L. HAMMEN (eds.) pp. 187-216 (Guilford Press, New York, 2008)). Compounding this problem, for depression, is that no real new drug class has entered clinical use in the last 40 years (E. J. Nestler. *Antidepressant Treatments in the 21$^{st}$ Century*, 44 Biol. Psych. 526-33 (1998)). However, recent studies have indicated that low-doses of the N-Methyl-D-aspartate (NMDA) receptor antagonist ketamine produce rapid antidepressant effects in treatment-resistant depression (R. M. Berman et al. *Antidepressant effects of ketamine in depressed patients*, 47 Biol. Psychiatry 351-4 (2000); C. A. Zarate et al. *A randomized trial of an N-methyl-D-aspartate antagonist in treatment-resistant major depression*, 63 Arch. Gen. Psychiatry 856-64 (2006)), defined as being insensitive to two classes of FDA-approved antidepressants and depression with suicidal ideation (R. B. Price et al. *Effects of Intravenous Ketamine on Explicit and Implicit Measures of Suicidality in Treatment-Resistant Depression*, 66 Biol. Psychiatry 522-(2009)). Increases in success rates for the treatment of these and other syndromes rely, in part, on the discovery of novel pharmacotherapeutics in clinically relevant animal models and screening assays.

Rodent-based models have long been the mainstay in behavioral pharmacology research and there exist a number of screening assays to detect anxiolytic or antidepressant activity of novel drug candidates. However, rodent models can be labor-intensive and time consuming, are typically expensive to conduct, fail to model the diverse clinical features of depression including co-morbidity with anxiety disorders, and may demonstrate weak treatment or drug effects, or worse, suffer from false positives and false negatives.

Research from this laboratory has developed an in vivo high utility, high-throughput model for screening anxiolytic drugs in domestic fowl chicks (K. J. Sufka et al. *Construct Validation of Behavioral Indices of Isolation Stress and Inflammatory Nociception in Young Domestic Fowl*, 55 Physiol. Behav. 741-46 (1994); G. S. Watson et al. *Chlordiazepoxide Reverses Social-Separation-Induced Distress Vocalizations and Analgesia in Young Domestic Fowl*, 4 Exp. Clin. Psychopharm. 347-53 (1996)). Using separation-induced distress vocalizations (DVocs) to index anxiety (G. S. Watson et al. 1996, supra), my laboratory has developed a set of procedures that allows for preclinical anxiolytic drug efficacy screening. (M. W. Feltenstein et al. *The Chick Separation Stress Paradigm: A Validation Study*, 77 Pharmacol. Biochem. Behav. 221-26 (2004); M. W. Feltenstein et al. *Anxiolytic Properties of Piper Methysticum Extract Samples and Fractions in the Chick Social-Separation-Stress Procedure*, 17 Phytother. Res. 210-16 (2003)). The chick separation stress paradigm possesses construct validity as an anxiety model in that separation stress reliably increases corticosterone levels (M. W. Feltenstein et al. *Dissociation of Stress Behaviors in the Chick Social-Separation-Stress Procedure*, 75 Physiol. Behav. 675-79 (2002)), a neuroendocrine marker of many stress responses. The model possesses predictive validity through the successful detection of diverse classes of anxiolytics (i.e., meprobamate, pentobarbital, chlordiazepoxide, imipramine and clonidine; (M. W. Feltenstein et al. 2004, supra), and is sensitive to potency differences within an anxiolytic class (i.e., alprazolam, lorazepam and chlordiazepoxide; (G. S. Watson et al. *Benzodiazepine Receptor Function in the Chick Social-Separation-Stress Procedure*, 7 Exp. Clin. Psychopharm. 83-89 (1999)). Furthermore, the model is insensitive to a wide range of nonanxiolytic compounds (i.e., amphetamine, scopolamine, caffeine, chlorpromazine, and haloperidol; (M. W. Feltenstein et al. 2004, supra). Finally, this paradigm has been used to identify anxiolytic activity in botanical extracts, extract fractions and isolated constituents in products marketed to consumer (K. J. Sufka et al. *Anxiolytic Properties Of Botanical Extracts In The Chick Social Separation-Stress Procedure*, 153 Psychopharm. 219-24 (2004)).

Domestic fowl chicks have also been used to model depression. (E. Lehr. *Distress Call Reactivation in Isolated Chicks: Behavioral Indicator With High Selectivity for Antidepressant Drugs*, 97 Psychopharm. 145-46 (1989)) reports that chicks isolated for two hours entered into what was described as a "learned helplessness" state, a behavioral profile commonly associated with depression. In this study, Lehr reports that a wide variety of putative antidepressant drugs reversed this learned helplessness state while those lacking antidepressant activity did not. Unfortunately, a fine-grained analysis of this work is all but impossible as very limited methodological details (e.g., use of total count of distress vocalizations for the two hour period) and resultant data (e.g., all data presented as drug dose values in mg/kg for either 150% or 50% effect of control) were published. Nevertheless, what can be ascertained from this two-page report is that this paradigm, I believe, most certainly conflates two or more clinical syndromes.

One current perspective among some clinical psychologists suggests that anxiety and major depression may represent a single syndrome that only differs in symptom severity and/or duration. This notion is based on significant overlap in signs and symptoms of the two disorders and co-morbidity rates of approximately 70% between anxiety and depression (R. C. Kessler et al. *Lifetime And 12-Month Prevalence Of DSM-III-R Psychiatric Disorders In The United States:*

*Results For The National Comorbidity Survey*, 51 Archives of General Psychiatry, 355-64 (1994)). However, no one has developed a pre-clinical drug-screening model that accurately displays homologies to the clinical features in depressive disorders of the co-morbidity of anxiety and depression in treatment-resistant subjects, which may account for a third or more of the clinical patient population.

SUMMARY OF THE INVENTION

This new animal model utilizes an inexpensive avian model, measures spontaneous behaviors in very young animals and is capable of detecting and/or differentiating a compound's anxiolytic and/or antidepressant effects. Animal costs are less than 10% of rodent costs and the assay can be run in a high-throughput mode. More specifically, this invention relates to a method to screen anxiolytic and antidepressant drugs in a plurality of fowl chicks with stress vulnerability. The steps of this method comprise: providing a plurality of fowl chicks, wherein a first portion of the fowl chicks receives at least one drug and a second portion of the fowl chicks do not receive the drug; audibly separating at least one fowl chick from the first portion and second portion of fowl chicks; detecting DVocs rate from the at least one separated fowl chicks at a first and second time; and comparing the DVocs rate of the at least one separated fowl chick from the first portion of fowl chicks and from the second portion of fowl chicks at a first and second time to screen for anxiolytic and antidepressant drugs. Preferably, the model is used to screen for antidepressant drugs for treating treatment-resistant depression.

This invention also relates to a method of identifying a candidate agent for treating treatment-resistant depression comprising the steps of: providing an experimental animal model of treatment-resistant depression; administering a candidate compound to at least one animal of the animal model; and evaluating one or more clinical parameters of treatment-resistant depression in the at least one animal of the animal model, wherein a candidate compound that is associated with an improvement in a clinical parameter of treatment-resistant depression is a candidate agent for the treatment of treatment-resistant depression. Preferably, the animal model comprises Black Australorp chicks.

Additionally, this invention relates to a system to screen for anxiolytic and antidepressant drugs. The system includes the elements: a plurality of fowl chicks with stress vulnerability, wherein a first portion of the plurality of fowl chicks receives at least one drug and a second portion of the plurality of fowl chicks that do not receive the at least one drug; means to audibly separate a fowl chick from the first portion of fowl chicks and from the second portion of fowl chicks; means to determine DVocs rate of the fowl chick from the first portion of fowl chicks and from the second portion of fowl chicks at a first and second time; and means to compare DVocs rate of the fowl chick from the first portion of fowl chicks and from the second portion of fowl chicks to screen for anxiolytic and antidepressant drugs. Preferably, the system is used to screen for antidepressant drugs for treating treatment-resistant depression.

BRIEF DESCRIPTION OF THE DRAWINGS

A more complete understanding of the invention and its advantages will be apparent from the following Description of the Preferred Embodiment(s) taken in conjunction with the accompanying drawings, wherein:

FIG. 19A shows imipramine doses of 0 to 20 mg/kg. * indicates a significant difference in DVoc rates in Production Reds compared to the vehicle group at 5 mg/kg imipramine (p<0.05). FIG. 19B shows fluoxetine doses of 0 to 10 mg/kg. No significant difference was detected for any doses tested. FIG. 19C shows maprotiline doses of 0 to 10 mg/kg. * indicates a significant difference in DVoc rates in Production Reds compared to the vehicle group at 2.5 and 5 mg/kg maprotiline ($p^s<0.05$) and in Black Australorps given 2.5 mg/kg maprotiline (p<0.05). FIG. 19D shows ketamine doses of 0 to 15 mg/kg. * indicates a significant difference in DVoc rates in Black Australorps compared to vehicle group given 10 mg/kg ketamine (p<0.05). Vehicle groups not shown. Sample sizes were n=9-12.

DETAILED DESCRIPTION OF THE INVENTION

Figure 1:
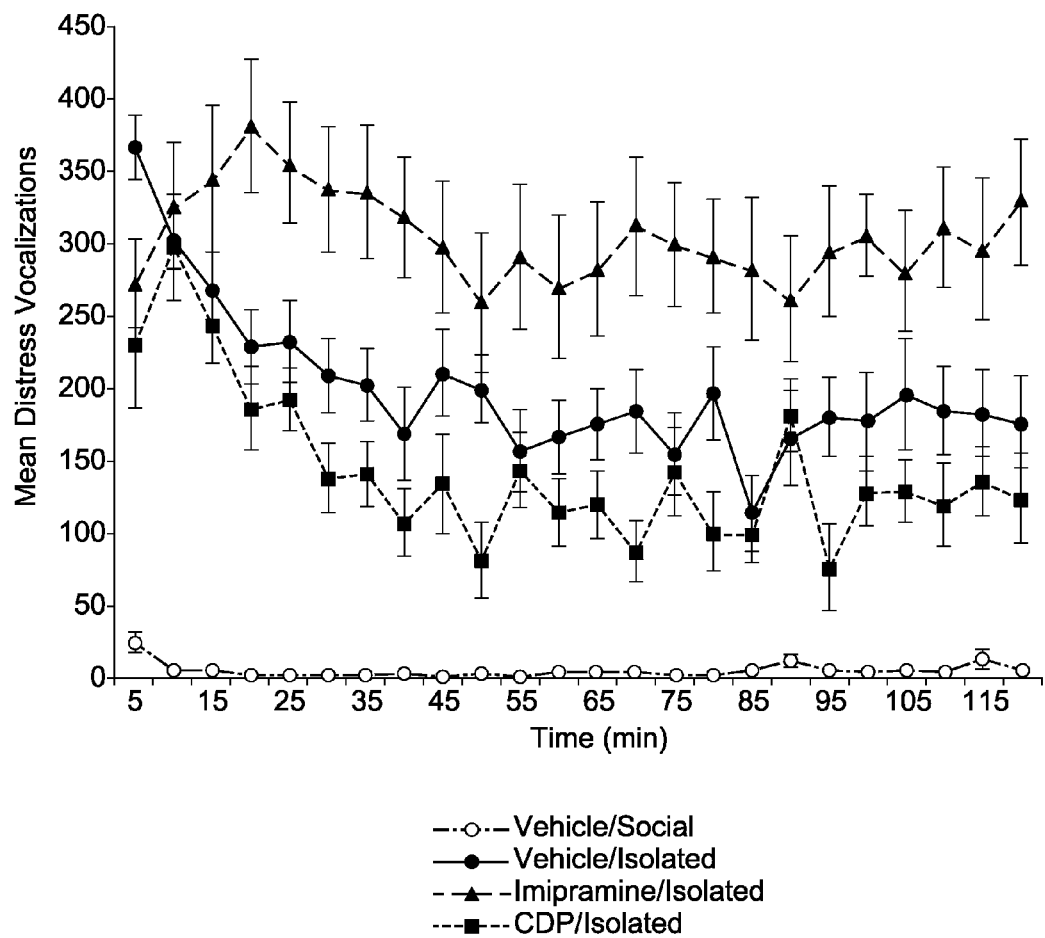
FIG. 1 shows the effects of imipramine (15 mg/kg) and chlordiazepoxide (8 mg/kg) on mean distress vocalizations (±SEM) over a 120-minute. test period. Open symbols represent social test condition and closed symbols represent isolated test condition. Sample sizes were n=12.

The present invention provides a high utility in vivo anxiolytic/antidepressant screening assay, one that models both anxiety and depression that mimic clinical presentation of treatment-resistant subjects or patients. More specifically, the invention provides a method to screen for anxiolytic and antidepressant drugs. The present model uses fowl chicks with stress vulnerability. Fowl chicks in the preferred embodiment are *Gallus gallus* with stress vulnerability. In a more preferred embodiment, the fowl chicks are of the Black Australorp strain. A first portion of the plurality of fowl chicks receive at least one of the drugs to be tested. A drug is an agent intended for use in the diagnosis, cure, mitigating treatment or prevention of a disease in a subject. The term drug includes botanical drugs and nonbotanical drugs. An anxiolytic is a drug used in the treatment of anxiety in a subject.

In the preferred embodiment, one of each class of drugs to be tested is administered to the first portion of fowl chicks. A second portion of fowl chicks do not receive the drug and function as the control. A fowl chick from the first and second portions is removed from the plurality of fowl chicks and placed in means to audibly separate the fowl chicks, such as a sound-attenuating enclosure. The DVoc rate for each of the audibly separated fowl chicks are determined by means such as microphones and electromagnetic counters. The DVoc rate is measured in the period that represents an anxiety state. In the preferred embodiment for the first 5 minutes, but this can range from 1 minute to 15 minutes. The DVocs rate is measured at a second period during the learned helplessness state which is akin to depression. In the preferred embodiment, the time is the 20-40 minute time block but can range from the 20-25 time block to 20-60 minute time block during the test session. The comparison of the DVoc rate from the fowl chicks that received the drug(s) with the control provides a high-throughput model for screening anxiolytic and antidepressant drugs.

In Example 1, the pattern of distress vocalizations in response to social separation is characterized to show that both anxiety and depression can be modeled in young domestic fowl. In addition, evidence is provided that the model can detect and differentiate both anxiolytic and antidepressant drug effects (i.e., predictive validity). In Example 2, the neuroendocrine marker of stress corticosterone is characterized throughout the test session as a measure of convergent validity of the stress model.

Young domestic fowl separated from conspecifics exhibit a stress response characterized by a variety of behaviors including distress vocalizations (DVocs: G. G. Gallup et al. *An Ethological Analysis Of Open-Field Behaviour In Chickens*, 28 Animal Behaviour, 368-78 (1980)). Conspecifics are animals of the same species. Distress vocalizations "DVocs" can be used to index anxiety (G. S. Watson et al. 1996, supra) and developed a set of procedures (chick separation stress paradigm) (M. W. Feltenstein et al. 2004, supra) that allows the model to be used as a high-utility, high-throughput, early pre-clinical in vivo anxiolytic screening assay (M. W. Feltenstein et al. 2004, supra). The model possesses construct validity as an anxiety model in that separation stress reliably increases corticosterone levels (M. W. Feltenstein et al. 2002, supra), a neuroendocrine marker of many stress responses. Additionally, the model possesses predictive validity through the successful detection of diverse classes of anxiolytics (i.e., meprobamate, pentobarbital, chlordiazepoxide, imipramine and clonidine; (M. W. Feltenstein et al. 2004, supra) and being sensitive to potency differences within an anxiolytic class (i.e., alprazolam, lorazepam and chlordiazepoxide; (G. S. Watson et al. 1999, supra). Furthermore, the model is insensitive to a wide range of nonanxiolytic compounds (i.e., amphetamine, scopolamine, caffeine, chlorpromazine, and haloperidol; (M. W. Feltenstein et al. 2004, supra).

The effects of the two drug probes on separation-induced DVocs are summarized in FIG. 1. Vehicle chicks tested in the presence of two social companions exhibited few, if any, DVocs during the course of the test session. Isolation from social companions produced a robust DVoc response in vehicle chicks. The rate of DVocs declined over the first 30 minute of the test session to approximately 50% of the initial response rate and remained relatively stable thereafter. At the five minute block, both chlordiazepoxide and imipramine attenuated DVocs. However, at the 20 minute block and beyond, where vocalization rates had declined, imipramine enhanced DVoc rates. During this same time period chlordiazepoxide did not generally alter DVoc rates from that of isolated chicks.

Consistent with these descriptions, a two-way ANOVA revealed significant main effects for Treatment [$F(3, 1012)=33.44, p<0.0001$], Time [$F(23, 1012)=7.67, p<0.0001$], and a significant Treatment×Time interaction [$F(69, 1012)=2.59, p<0.0001$]. A one-way repeated measures for the vehicle-social group revealed a significant effect for Time [$F(23, 253)=3.46, p<0.0001$]. Post hoc analyses demonstrated that the only consistent and relevant difference in DVoc rates across time blocks was that chicks vocalized significantly more in the first five minute than each of the remaining test session blocks ($p^s<0.005$). To examine the ontogeny of learned helplessness, a one-way repeated measures for the vehicle-isolated group was performed and revealed a significant effect for Time [$F(23, 253)=7.36, p<0.0001$]. The results of post hoc analyses highlight three noteworthy patterns. First, DVocs were highest at the five minute time block and significantly lower for each of the remaining test session blocks ($p^s<0.05$). Second, there were no difference in DVoc rates between the 10 and 15 minute time blocks or the 15 and 20 minute time blocks as DVoc rates gradually declined; DVoc rates for the 30-120 portion of the test session were significantly lower than the 5-15 minute period ($p^s<0.05$). Finally, DVoc rates were generally stable across the 20-120 minute portion of the test session ($p^s<0.05$).

To examine the effects of the drug probes on patterns of DVocs, one-way ANOVAs were conducted at various test intervals. A one-way ANOVA at the first five minute time block revealed a significant treatment effect [$F(3, 44)=24.53, p<0.0001$]. Post hoc analyses demonstrated that the vehicle-isolated group vocalized significantly more than the vehicle-social group and that imipramine and chlordiazepoxide significantly reduced distress vocalizations in isolated groups (all $p^s<0.0001$). One way ANOVAs at the 10 minute [$F(3, 44)=25.40, p<0.0001$] and 15 minute [$F(3, 44)=21.50, p<0.0001$] time blocks revealed significant treatment effects. In both sets of analyses, post hoc tests demonstrated that distress vocalizations were significantly higher in all three isolated groups compared to the vehicle-social group ($p^s<0.0001$); no other relevant comparisons (i.e., effects of drug probes) reached statistical significance.

A one-way ANOVA at the 20 minute time block revealed a significant treatment effect [$F(3, 44)=27.24, p<0.0001$]. Post hoc analyses demonstrated that while vehicle-isolated DVoc rates had declined from their initial rate they were still significantly higher than vehicle-social chicks ($p<0.0001$). Interestingly, the decline in DVoc rates in vehicle-isolated chicks was reversed in chicks receiving imipramine ($p<0.0001$); chlordiazepoxide did not affect DVoc rates at this time block. In general, this pattern of treatment effects on DVoc rates remained consistent throughout the remainder of the test session [e.g., at 60 minute, $F(3, 44)=13.46, p<0.0001$ and at 120 minute, $F(3, 44)=17.97, p<0.0001$].

Distress vocalizations in the vehicle-social condition were at or below 25 DVocs/five minute block and remained stable throughout the two hour test session (see FIG. 1). In vehicle-isolated chicks, distress vocalizations exceeded 350 vocalizations in the first five minute block, gradually declined over the 10-20 minute, and then stabilized between 150 and 200 DVocs per five minute block throughout the remaining portion of the testing session. Thus, the pattern of DVocs in isolated chicks is characterized by three components rather than two suggested by (E. Lehr 1989, supra) and includes initial protest, behavioral despair and learned helplessness. Distress vocalizations are maximal at the beginning of the testing session, marking the initial protest phase. The next component, I describe here as behavioral despair and is characterized by the notable decrease in distress vocalizations in the next 10-15 minute of social separation. The final component, learned helplessness, is characterized by a reduced and stable pattern of distress vocalizations and was observed for the remainder of the test session.

Both chlordiazepoxide and imipramine attenuated DVocs during the first five minute time block, the phase I refer to as the initial protest. These findings are consistent with previous work in my laboratory demonstrating that both anxiolytics and antidepressants possess anxiolytic properties in the chick separation stress paradigm (M. W. Feltenstein et al. 2004, supra). Imipramine, but not chlordiazepoxide, enhanced DVocs rates beyond the 15 minute block as the chicks entered into the learned helplessness phase of the social separation response. This pattern of drug effects is consistent with the clinical literature in which anxiety states can be treated with either anxiolytics or antidepressants while depression is treated with only antidepressants and is unresponsive to anxiolytic classes of drugs. Taken together, these data argue that 1) the increase in DVocs during the initial protest represents an anxiety state that is sensitive to drug probes that possess anxiolytic properties and 2) diminished DVoc rates represents a learned helplessness state akin to depression that is sensitive to drug probes that possess antidepressant properties.

In Examples 3 and 4 a series of drug probes were used to test the efficacy of clinically established anxiolytics (i.e., chlordiazepoxide and clonidine) and anxiolytic/antidepressants (i.e., imipramine, maprotiline and fluoxetine) and a biochemical assay of the plasma IL-6 concentrations across the test session. Across the drug probes, the vehicle/isolated chicks had a robust exacerbation of DVocs compared to the vehicle/social chicks during the anxiety-like phase of the test session (i.e., the first five min block). All of the compounds, with the exception of fluoxetine, attenuated DVocs during this phase. Also, across the drug probes, the mean DVocs in the vehicle/isolated condition decreased over the first fifteen min to approximately 60% of the initial five min time block, which then remained stable throughout the test session (i.e., the depression-like phase). All of the anxiolytic/antidepressant compounds (i.e., imipramine, maprotiline and fluoxetine) were able to increase the mean number of DVocs within this phase of the test session.

Although fluoxetine has been shown in numerous experiments to be a clinically efficacious anxiolytic (J. M. Gorman et al. *An Open Trial of Fluoxetine in the Treatment of Panic Attacks*, 7 J. Clin. Psychopharmacol. 329-32 (1987); D. Michelson et al. *Outcome Assessment and Clinical Improvement in Panic Disorder: Evidence From a Randomized Controlled Trial of Fluoxetine and Placebo*, 155 Am. J. Psychiatry 1570-7 (1998); D. Michelson et al. *Continuing Treatment of Panic Disorder after Acute Response: Randomized, Placebo-Controlled Trial With Fluoxetine*, 174 Br. J. Psychiatry 213-08 (1999)), it is not surprising it did not attenuate DVocs during the anxiety-like phase of the test session due to the drug's strong serotonin reuptake inhibition (R. W. Fuller, D. T. Wong. *Inhibition of Serotonin Reuptake*, 36 Fed. Proc. 2154-8 (1977)). Serotonin release in the medio-rostral neostriatum/hyperstriatum ventrale has been found to be involved in the production of separation DVocs (K. Baldauf et al. *Opiate Modulation of Monoamines in the Chick Forebrain: Possible Role In Emotional Regulation?* 62 J. Neurobiol. 149-63 (2005)). While an argument can be made that not detecting fluoxetine represents a partial false negative for the model, it is also possible that the lack of effect may actually help further characterize the model's anxiety-like phase. A recent study in this laboratory demonstrated that the chick separation stress paradigm selectively detected drugs efficacious in the treatment of panic disorder (i.e., phenelzine, imipramine, alprazolam, and clonidine) and was insensitive to drugs selectively efficacious in treating generalized anxiety disorder (i.e., buspirone and trazodone; J. E. Warnick et al. *Modeling Anxiety-Like States: Pharmacological Characterization of the Chick Separation Stress Paradigm*, 17 Behav. Pharmacol. 581-7 (2006)). While fluoxetine has been used clinically for the treatment of panic disorder (J. M. Gorman et al. supra; D. Michelson et al. (1998), supra; D. Michelson et al. (1999), supra), it has been shown to be ineffective in the treatment of situationally-bound panic disorder (E. H. Uhlenhuth et al. *Do Antidepressants Selectivity Suppress Spontaneous (Unexpected) Panic Attacks? A Replication*, 20 J. Clin. Psychopharmacol. 622-7 (2000)). It is possible that instead of being a false negative, fluoxetine further defines the anxiety-like phase as modeling situationally-bound panic disorder.

The pattern of drug effects found in the current experiment help to further establish the face validity of this system. The system was able to 1) detect all of the investigatory anxiolytic agents that are efficacious for situationally-bound panic disorder (i.e., clonidine, chlordiazepoxide, imipramine & maprotiline), 2) detect all of the investigatory antidepressant agents (i.e., imipramine, maprotiline, and fluoxetine), and 3) show discriminate validity as the anxiolytics did not show antidepressant activity. Further, the efficacy of the antidepressants show a pattern similar to that found in humans. The dosage and clinical efficacy of imipramine, fluoxetine and maprotiline have been found to be virtually identical in humans (Baldessarini. *The Pharmacological Basis of Therapeutics*, (10th Ed.) J. G. Hardman & L. E. Limbird (eds.); pp. 447-83 (McGraw-Hill, New York, 2001); C. M. Beasley et al. *Fluoxetine Compared With Imipramine In The Treatment of Inpatient Depression. A Multicenter Trial*, 5 Ann. Clin. Psychiatry 199-07 (1993); F. de Jonghe et al. *A Randomized, Double-Blind Study of Fluoxetine and Maprotiline in the Treatment of Major Depression*, 24 Pharmacopsychiatry 62-7 (1991); J. N. Logue et al. *Comparisons of Maprotiline With Imipramine in Severe Depression: A Multicenter Controlled Trial*, 19 J. Clin. Pharmacol. 64-74 (1979); B. M. Nielsen et al. *A Comparison of Fluoxetine and Imipramine in the treatment of Outpatients With Major Depressive Disorder*, 87 Acta. Psychiatr. Scand. 269-72 (1993); B. G. Wells et al. *Chemistry, Pharmacology, Pharmacokinetics, Adverse Effects, and Efficacy of the Antidepressant Maprotiline Hydrochloride*, 1 Pharmacotherapy 121-39 (1981)). A comparison of the $ED_{50}(CI_{95})$ values of these compounds in the current model reveal virtually identical drug effects across the three compounds (Table 1). In addition to furthering the face validity, these findings also provide some preliminary evidence of the model possessing construct validity. That is, similarities in pharmacological profiles suggest similarities in neurobiology (Behavioural Models in Psychopharmacology: Theoretical, Industrial and Clinical Perspectives, Willner P. (ed.) pp. 3-18 (Cambridge University Press, Cambridge, 1991)).

TABLE 1

Experiment 1: $ED_{50}$ and $CI_{95}$ Values for the Antidepressant (AD) Effect of Clinically Efficacious Compounds.

|  | AD Effect (20-40 min time block) | AD Effect (40-60 min time block) | AD Effect (60-80 min time block) | AD Effect (80-100 min time block) | AD Effect (100-120 min time block) |
|---|---|---|---|---|---|
| Imipramine |  |  |  |  |  |
| $ED_{50}$ | N/A | 10.0 | 8.5 | 9.1 | 7.6 |
| $CI_{95}$ | N/A | 7.8-13.9 | 6.7-11.6 | 7.0-13.0 | 5.9-10.7 |
| Maprotiline |  |  |  |  |  |
| $ED_{50}$ | 17.2 | 14.0 | 14.9 | 13.6 | 14.6 |
| $CI_{95}$ | 12.9-25.7 | 10.7-20.2 | 11.4-21.7 | 10.4-19.8 | 10.9-22.1 |

TABLE 1-continued

Experiment 1: $ED_{50}$ and $CI_{95}$ Values for the Antidepressant (AD) Effect of Clinically Efficacious Compounds.

| | AD Effect (20-40 min time block) | AD Effect (40-60 min time block) | AD Effect (60-80 min time block) | AD Effect (80-100 min time block) | AD Effect (100-120 min time block) |
|---|---|---|---|---|---|
| Fluoxetine | | | | | |
| $ED_{50}$ | N/A | 16.5 | 13.3 | 14.0 | 14.0 |
| $CI_{95}$ | N/A | 12.9-25.7 | 10.4-18.6 | 10.7-20.0 | 10.8-19.8 |

In the biochemical assay, plasma IL-6 concentration was found to change during the course of the test session (i.e., increased concentration at 120 min of social separation). Clinical studies have shown that major depression is associated with increased levels of cytokines, including elevated plasma IL-6 concentrations (J. L. Pike et al. *Dissociation of Inflammatory Markers and Natural Killer Cell Activity In Major Depressive Disorder*, 49 Psychiatry 13-6 (2006)). Animal models of depression have displayed equivocal results with most showing no change in plasma IL-6 (A. J. Dunn et al. *Cytokines As Mediators of Depression: What Can We Learn from Animal Studies?*, 29 Neurosci. Biobehav. (2005); e.g., chronic mild stress: C. Mormède et al. *Chronic Mild Stress in Mice Decreases Peripheral Cytokine and Increases Central Cytokine Expression Independently of IL-10 Regulation of the Cytokine Network*, 10 Neuroimmunomodulation 359-66 (2003)) and a limited number of showing increases (e.g., restraint stress depression model: D. Zhou et al. *Exposure to Physical And Psychological Stressors Elevates Plasma Interleukin 6: Relationship to the Activation of Hypothalamic-Pituitary-Adrenal Axis*, 133 Endocrinology 2523-30 (1993)). Thus, the ability of the model to increase plasma IL-6 levels not only provides evidence of the model's construct validity, it sets it apart from the depression models that are unable to produce such neuroimmunological changes.

It should be noted that the increased plasma concentration of IL-6 could also be indicative of processes other than that accompanying depressive symptomology. For example, in humans, IL-6 has been shown to be elevated in response to sustained physical activity (H. Northoff et al. *Immunologic Mediators as Parameters of the Reaction to Strenuous Exercise*, 12 Int. J. Sports. Med. S9-S15 (1991)). It is possible that the elevated concentration of IL-6 found in the current study could be the result of the two hours of persistent DVocs.

My laboratory compared nine diverse genetic lines in the model and identified two strains in which one displayed stress vulnerability (Black Australorp) and the second stress resilience (Production Red) as measured by onset of behavioral despair (K. A. Hymel, M. J. Lorea, A. L. Salmeto, S. W. White, K. J. Sufka. *The sky is falling; strain vulnerability and resiliency in the chick anxiety depression model*, Annual Meeting of the Society for Neuroscience (New Orleans, La. Oct. 13-17, 2012)). In Example 5, I sought to explore whether these two lines display differential sensitivities to antidepressant compounds by screening the tricyclic antidepressant (TCA) imipramine, the selective norepinephrine reuptake inhibitor (SNRI) maprotiline, the selective serotonin reuptake inhibitor (SSRI) fluoxetine, and the NMDA receptor antagonist ketamine. Doses selected were based on my laboratory's published studies using our anxiety-depression model (J. E. Warnick, C.-J. Huang, E. O. Acevedo, K. J. Sufka. *Modelling the anxiety-depression continuum in chicks*, 23 J. Pyschopharmacol. 143-156 (2009); K. J. Sufka et al. *Antidepressant efficacy screening of novel targets in the chick anxiety-depression model*, 20 Behav. Pharmacol. 146-154 (2009)). Surprisingly, I discovered that the stress-vulnerable line displays similar homology to antidepressants as patients diagnosed with treatment-resistant depression.

Figure 18:
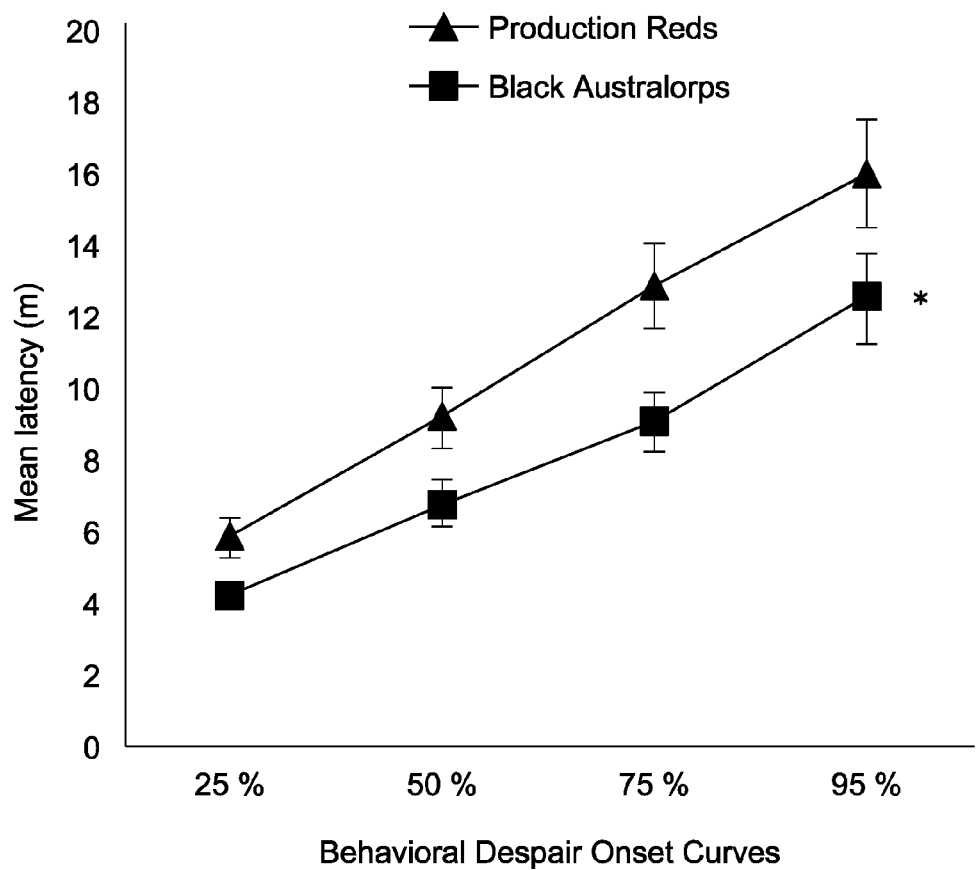
FIG. 18 shows mean latency as a function of the onset of behavioral despair between vehicle-isolated Production Red and Black Australorp chicks. Triangle symbols represent Production Red strain chicks and square symbols represent Black Australorp strain chicks. Values represent mean (±SEM) minutes. * indicates a significant difference between strains across the behavior onset curve (p=0.012). Sample sizes were n=9-12. This graph highlights the stress vulnerability and stress resiliency across the Black Australorp and Production Red strains, respectively.

To highlight stress vulnerability and resiliency across strains, I then calculated the onset of behavioral despair in vehicle-isolated chicks by determining the time at which a chick's individual DVoc rate declined 25%, 50%, 75%, and 95% to the rate during its depression-like phase (see FIG. 18). Compared to the Production Red line, Black Australorps displayed significantly shorter latencies across the thresholds in their behavioral despair onset curve.

Figure 19A:
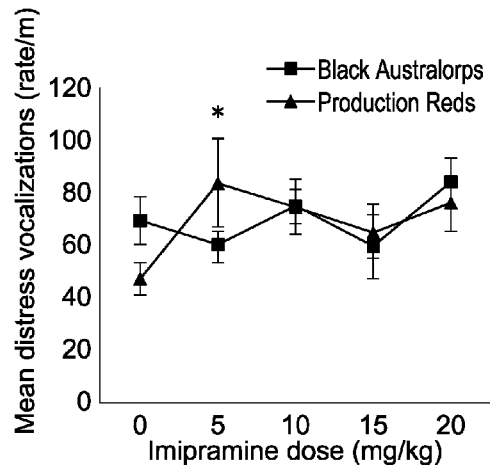
FIG. 19A-D show the effects of four classes of anti-depressant drugs on mean distress vocalization rate/min (±SEM) as a function of drug dose during the depression-like phase of the model (30-90 min) in isolated 5-6 day old chicks from the Production Red and Black Australorp strains. Triangle symbols represent Production Red strain chicks and square symbols represent Black Australorp strain chicks.
Figure 19B:
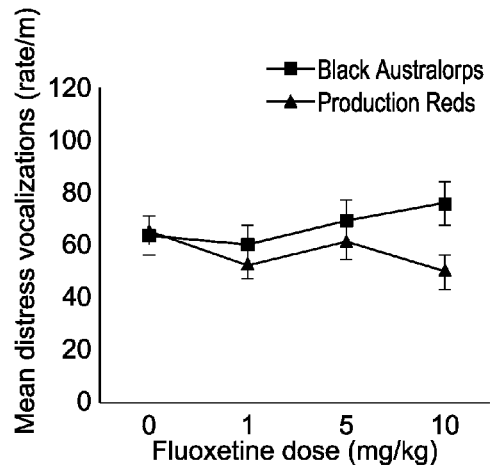
Figure 19C:
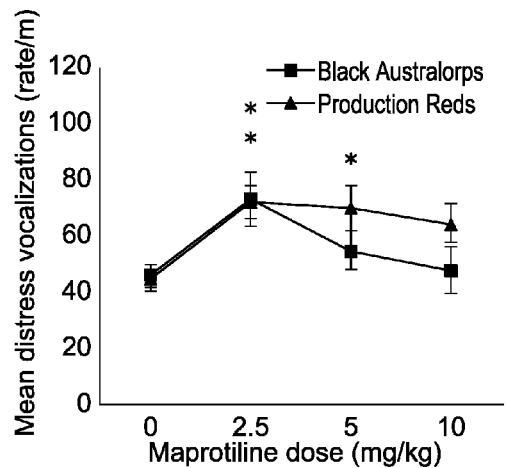
Figure 19D:
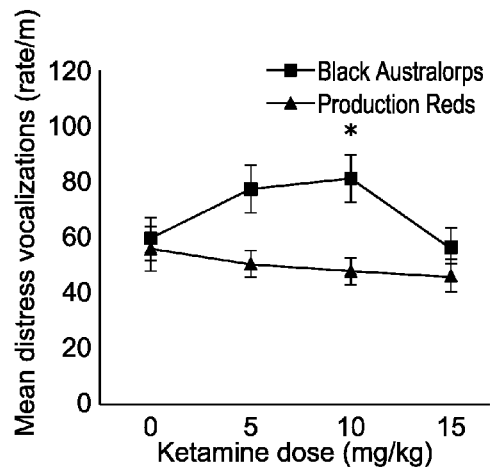

In previous research antidepressants have been shown to attenuate behavioral despair in the chick social separation stress model as indexed by an increase in DVoc rates during the depression-like phase (K. J. Sufka, M. W. Feltenstein, J. E. Warnick, E. O. Acevedo, H. E. Webb, C. M. Cartwright. *Modeling the anxiety-depression continuum hypothesis in domestic fowl chicks*, 17 Behav. Pharmacol. 681-9 (2006); J. E. Warnick et al. 2009, supra; E. Lehr 1989, supra). To illustrate differential sensitivities to antidepressants between Production Reds and Black Australorps, dose response curves for each drug probe are summarized in FIGS. 19A and B. Imipramine possessed antidepressant activity as indexed by a significant increase in DVoc rate in the Production Reds at the 5 mg/kg dose. However, imipramine failed to alter DVoc rates in the Black Australorps at any dose tested (see FIG. 19A). Fluoxetine failed to show antidepressant effects at any dose tested in either strain (see FIG. 19B). Maprotiline produced an antidepressant effect at 2.5 and 5.0 mg/kg in Productions Reds and at 2.5 mg/kg in Black Australorps (see FIG. 19C). Ketamine failed to affect DVoc rates in Production Reds but did show significant antidepressant activity at the 10 mg/kg dose in Black Australorps (see FIG. 19D). A follow-up study with ketamine at lower doses failed to see antidepressant activity in either strain noting the highest dose tested produced transient (5-10 min) ataxia (data not shown).

A summary of these findings alongside that of previously published screening studies of the drug probes in a White Leghorn strain is detailed in Table 2 (J. E. Warnick et al. 2009, supra; K. J. Sufka et al. Behav. Pharmacol. 2009, supra). The stress-resilient Production Red line displayed sensitivity to two classes of FDA-approved antidepressants but were insensitive to fluoxetine and ketamine. This pattern is somewhat surprising as I expected to see sensitivity to all four compounds given earlier findings that these same drug probes within the same dose range possessed antidepressant activity in a White Leghorn strain albeit from a different vendor. That the Production Red strain a) is stress-resilient and b) fails to respond to all test probes, particularly ketamine, suggest this may not be a useful strain for broad use antidepressant preclinical screening.

TABLE 2

| Drug Probe | Fowl Strain | | |
|---|---|---|---|
| | White Leghorns | Production Reds (stress-resilient) | Black Australorps (stress-vulnerable) |
| Imipramine | + | + | − |
| Fluoxetine | + | − | − |
| Maprotiline | + | + | + |
| Ketamine | + | − | + |

In contrast to the Production Reds and White Leghorns, the stress-vulnerable Black Australorp line failed to show antidepressant sensitivity to imipramine and fluoxetine at the broad range of doses tested. This line did show antidepressant sensitivity to maprotiline at a limited dose range. This pattern of drug effects meets the clinical criteria of being treatment-resistant because of the insensitivity to two classes of antidepressants. Interestingly, this stress-vulnerable, treatment-resistant Black Australorp line shows sensitivity to ketamine. This finding parallels the clinical picture in that treatment-resistant depression responds well to ketamine after a single administration. That the Black Australorp strain is a) stress-vulnerable, b) treatment-resistant (fails two drug probes) and c) ketamine sensitive, and these data suggest that this line is the first animal model for pre-clinical screening of novel antidepressants for use in treatment-resistant depression.

The underlying mechanisms that differentiate drug response between chick genetic lines are unknown at this time. Like rodent models, I hypothesize that insensitivity to fluoxetine involves altered expression of the serotonin transporter protein (A. M. Carneiro, D. C. Airey, B. Thompson, C.-B. Zhu, E. J. Chesler, K. M. Erikson, R. D. Blakely. *Functional coding variation in recombinant inbred mouse lines reveals multiple serotonin transporter-associated phenotypes,* 106 Proc. Natl. Acad. Sci. 2047-52 (2009)). Such strain comparison research may not only identify CNS markers that differentiate drug sensitivity but also stress-vulnerability/resiliency in these lines. For example, recent research points to the SLC6A15 gene that affects amino acid transporters and, interestingly, confers stress vulnerability in animal models (M. A. Kohli, et al. *The neuronal transporter gene SLC6A15 confers risk to major depression,* 70 Neuron 252-65 (2011)). Further, studies in the Black Australorp line could lead to the identification of new targets for treatment-resistant depression.

A body of evidence argues that depression reflects stunted neurogenesis in homeostatic networks that respond to stress (R. S. Duman, G. K. Aghajanian. *Synaptic dysfunction in depression: potential therapeutic targets,* 338 Science 68-72 (2012); A. J. Eisch, D. Petrik. *Depression and Hippocampal Neurogenesis: A Road to Remission?,* 338 Science 72-75 (2012)). Interestingly, ketamine's rapid clinical effects are thought mediated by potentiation of α-amino-3-hydroxy-5-methyl-4-isoxazolepropionic acid (AMPA) receptors that elevate BDNF via the mammalian target of rapamycin (mTOR) pathway. BDNF acts on tyrosine kinase B (TrkB) receptors to produce neurogenesis, specifically Arc-mediated expansion and stabilization of spines and expression of glutamate A1 receptors, in a neural homeostatic control system that respond to stress events (A. J. Eisch & D. Petrik. supra; A. R. Santos, D. Comprido, C. B. Duarte, *Regulation of local translation at the synapse by BDNF,* 92 Prog. Neurobiol. 505-516 (2010)). Recent studies in my lab quantifying hippocampal BDNF in these two chick lines ties nicely into this neurogenesis hypothesis of depression (M. J. Loria, S. W. White, S. A. Robbins, A. L. Salmeto, K. A. Hymel, S. N. Murthy, P. Manda, K. J. Sufka. *Brain-derived neurotrophic factor response in vulnerable and resilient genetic lines in the chick anxiety-depression model,* 245 Behav. Brain Res. 29-33 (2013)). No differences in BDNF levels were observed prior to stress exposure. The resilient Production Red line showed stable BDNF levels throughout the isolation stress period whereas the vulnerable Black Australorp line showed elevated BDNF that peaked at 90 minutes into the test period and declined thereafter. I interpreted these finding to suggest that stress vulnerability reflects a loss of homeostatic control mechanisms involved in synaptogenesis.

Animal models have been useful in understanding the underlying neurobiological mechanisms of depression. There exist a number of modified rodent lines that show stress-vulnerability and include, for example, the inbred rat Wistar-Kyoto line (A. Lahmame, A. Armario. *Differential responsiveness of inbred strains of rats to antidepressants in the forced swimming test: are Wistar Kyoto rats an animal model of subsensitivity to antidepressants?,* 123 Psychopharmacol. 191-198 (1996)) and the mouse val66met knock-in model of the human variant loss-of-function BDNF gene (J. M. Gatt et al. *Interactions between BDNF Val66Met polymorphism and early life stress predict brain and arousal pathways to syndromal depression and anxiety,* 14 Mol. Psychiatry. 681-695 (2009)). The Wistar-Kyoto line has also shown sensitivity to ketamine (Y. Tizabi, B. H. Bhatti, K. F. Manaye, J. R. Das, L. Akinfiresoye. *Antidepressant-like effects of low ketamine dose is associated with increased hippocampal AMPA/NMDA receptor density ratio in female Wistar-Kyoto rats,* 213 Neurosci. 72-80 (2012)). However, to my knowledge, no antidepressant screening paradigm has shown to be a stress-vulnerable, treatment-resistant, ketamine-sensitive simulation of depression. The Black Australorp line in the chick anxiety-depression model is the first screening tool for identifying promising treatment strategies for individuals with major depression who fail to respond to current therapies.

EXAMPLE 1

Subjects. Cockerels (*Gallus gallus*, strain W-36; Cal-Maine Foods, Mendenhall, Miss., USA) were obtained 1 day posthatch and housed in stainless steel cages (34×57×40 cm) at a population density of 12 chicks per cage. Food (Purina Start and Grow, St. Louis, Mo., USA) and water were available ad libitum through a 1-quart gravity-fed feeders and waterers. Room temperature was maintained at 29+1° C. and overhead florescent illumination was maintained on a 12-h light-dark cycle provided by fluorescent overhead lighting.

Apparatus. A six-unit test apparatus containing Plexiglas viewing chambers (25×25×22 cm) situated in sound-attenuating enclosures was used for behavioral data collection. The units were illuminated using 25-W light bulbs and ventilated by an 8-cmdiameter rotary fan. Miniature video cameras mounted at floor level in the corner of the enclosures allowed for animal observation. Microphones that mounted at the ceiling of the Plexiglas chamber were connected to digital sound-activating relays, which activated electromechanical counters. A white noise generator provided room masking noise.

Procedure. Tests were conducted at either Day 4, 5, or 6 posthatch. Groups formed a single factorial design with a hanging control that included two vehicle-control groups in which chicks were tested in either an isolated or social condition, and two drug groups under the isolation condition. The vehicle was 0.9% physiological saline and the drug probes were chlordiazepoxide (8 mg/kg) and imipramine (15 mg/kg). Sample sizes were n=12 per cell.

Vehicle and drug injection were administered IP 15 minute before tests. The stress manipulation involved placing a chick in the observation chamber in isolation or in the presence of two conspecifics (social test condition) for a 120 minute test period. The dependent measure of distress vocalizations (DVocs) was collected in five minute time blocks. Animals were returned to their home cage following tests. All experimental procedures complied with the NIH *Principles of Laboratory Animal Care* (NIH publication #86-23 1996) and were approved by the University of Mississippi IACUC (protocol #04-020).

Statistics. Data were analyzed using one- and two-way repeated measures analysis of variance (ANOVA) and one-way simple effects ANOVA. Post hoc analyses were conducted using Fisher's LSD.

EXAMPLE 2

Corticosterone is a biological marker of stress in animals and my laboratory have used this marker to provide convergent validity of the chick separation stress paradigm as a model of anxiety (M. W. Feltenstein et al. *Corticosterone Response In The Chick Separation-Stress Paradigm*, 78 Physiol. Behav. 489-93 (2003)). In Example 2, I attempt to provide evidence of convergent validity to the model by quantifying the pattern of corticosterone response in chicks during the three phases of the test session (i.e., initial protest, behavioral despair and learned helplessness). Because no appreciable changes were detected in DVoc rates during the last 90-100 minute, the test session was shortened to one hour in length in Example 2.

Subject and test apparatus were as described in Experiment 1. Tests were conducted 4-5 days posthatch and in the first third of the light portion of the 12:12 light-dark cycle. The experimental design consisted of 7 treatment conditions that included one social group (test length=60 minute) and six isolated groups (test lengths=5, 10, 15, 20, 40 and 60 minute). Sample sizes were n=12. Following behavioral data collection, half the subjects from each group were taken from the test apparatus and rapidly decapitated for blood collection. Prior to conducting behavioral tests, a no-test control group (no stress manipulation) was taken from their home cages for blood collection. All blood samples were collected in EDTA tubes and were immediately chilled. These procedures were approved by the University of Mississippi's IACUC (protocol #05-008).

Corticosterone Assay. Blood samples were centrifuged for 15 minute at 3000 rpm. Supernatants were collected and stored at −80° C. until analysis. Plasma corticosterone concentrations were determined by radioimmunoassay (Coat-a-Count RIA Kit: Diagnostic Products, Los Angeles, Calif.). The inter-assay coefficient of variations was 2.72%, the intra-assay coefficient was 1.84% and the $R^2$ of the standards was 0.982.

Statistical analyses. Statistical analyses one these data included one-way and two-way ANOVAs, Fisher's LSD, t-tests and Pearson's correlation.

Figure 2:
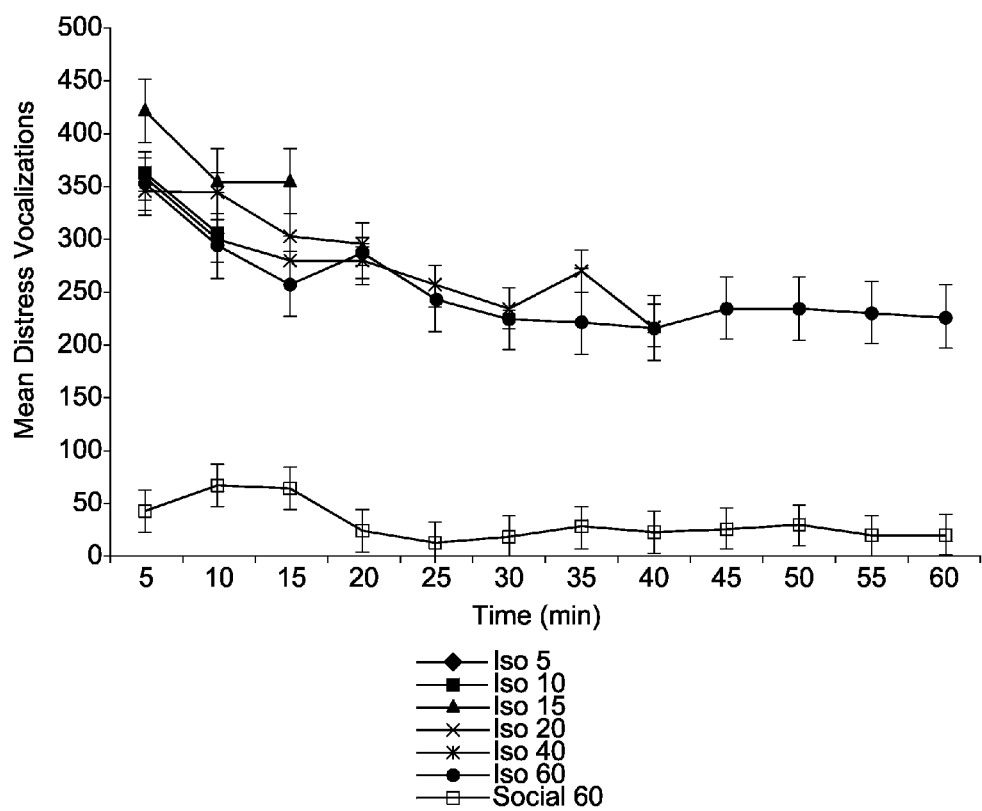
FIG. 2 shows the effects of varying lengths of isolation (Iso) from social companions on mean distress vocalizations (±SEM). Chicks tested in the presence of two conspecifics for 60 minutes (Social 60) are represented by open squares. Sample sizes were n=12.

The effects of varying lengths of social separation on DVocs are summarized in FIG. 2. In animals tested in the social condition, DVocs were infrequent and remained stable across the 60 minute test session. For all of the other test groups, isolation from conspecifics produced a robust elevation in DVocs. This increase in DVocs gradually declined over the initial 20 minute period by approximately 30-40%, marking the emergence of learned helplessness. Thereafter, DVocs remained relatively stable throughout the remainder of the test session.

A time course analysis of the vocalization data in the social- and isolated-60 minute groups nicely illustrates both the stress effect of social separation and the emergence of learned helplessness in isolated chicks. Thus, a two-way repeated measures ANOVA conducted for these two groups revealed a significant main effect for Treatment [$F(1,220)=78.51$, $p<0.0001$], a significant main effect for Time [$F(11, 220)=5.15$, $p<0.0001$], and a significant Treatment×Time interaction [$F(11, 220)=2.13$, $p<0.05$].

A one-way repeated measures for the vehicle-social group revealed a significant effect for Time [$F(11, 110)=1.91$, $p<0.05$]. Post hoc analyses demonstrated that the only consistent and relevant difference in DVoc rates across time blocks was that chicks vocalized significantly more at the 10 and 15 minute blocks than each of the other test session blocks ($p^s<0.05$). To examine the ontogeny of learned helplessness, a one-way repeated measures for the vehicle-isolated group was performed and revealed a significant effect for Time [$F(11,110)=4.29$, $p<0.0001$]. The results of post hoc analyses highlight three noteworthy patterns. First, DVocs were highest at the five minute time block and significantly lower for each of the remaining test session blocks ($p^s<0.05$). Second, there was no difference in DVoc between the 10, 15 and 20 minute time blocks as DVoc rates gradually declined. Finally, DVoc rates were stable across the 25-60 minute portion of the test session and these rates were significantly lower than the 5 and 10 minute blocks ($p^s<0.05$).

Figure 3:
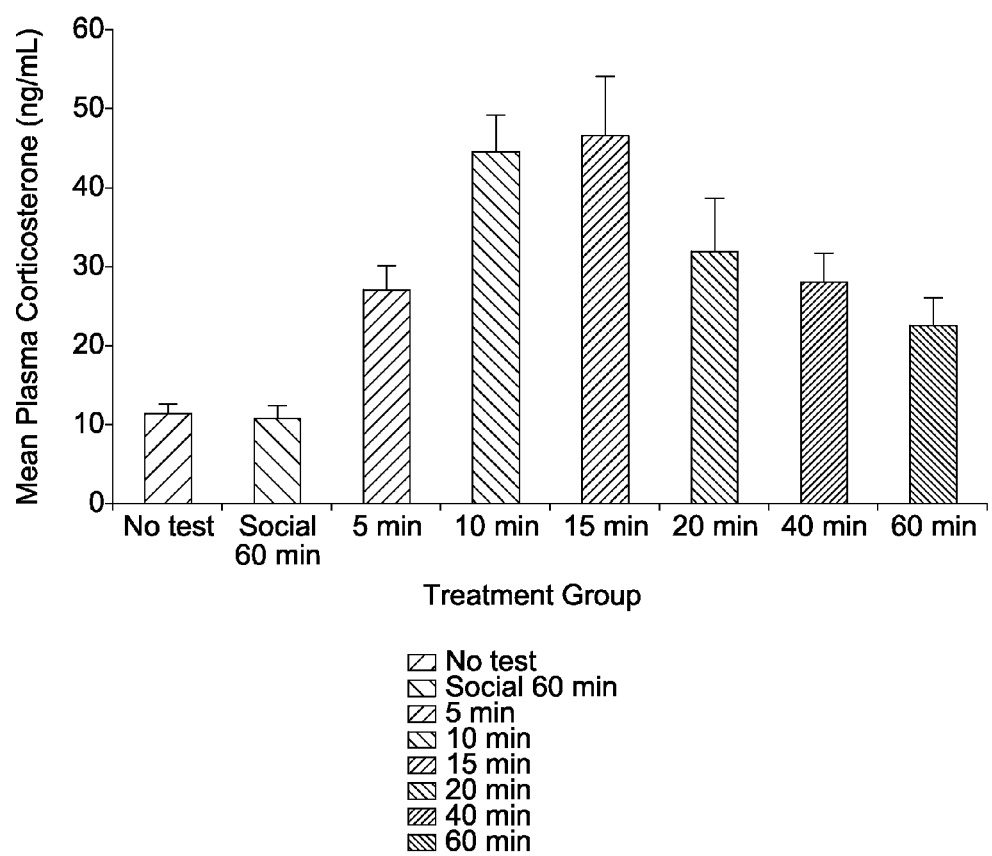
FIG. 3 shows the effects of varying lengths of social separation on mean (±SEM) plasma corticosterone concentration (ng/mL). In No-Test birds, blood was collected immediately after removal from home cages (hatched bar). Social birds were tested in the presence of two conspecifics for 60 minute and blood was collected immediately after testing (gray bar). Six groups of birds were tested in isolation for various time points (i.e., 5, 10, 15, 20, 40, and 60 minute.) and blood was collected immediately after testing (closed bars). Sample sizes were n=6.

The effects of varying lengths of social separation stress on plasma corticosterone are summarized in FIG. 3. Levels of corticosterone in the social-60 group were comparable to the no-test control group, averaging approximately 11 ng/mL. Levels of corticosterone in the isolated groups were elevated and averaged between 22 and 46 ng/mL. The pattern of this stress-induced corticosterone response was marked by a peak in the isolated-10 and -15 minute groups, and a gradual decline in the 20, 40 and 60 minute isolation conditions.

To examine the effects of exposure to the testing protocol as well as the effects of social separation on plasma corticosterone levels, a one-way ANOVA was conducted on these data in the No-Test, Social-60 and Isolation-60 groups. This analysis revealed a significant effect for Treatment, $F(2,14)=8.88$, $p<0.005$. Post hoc analyses of these data revealed that mean plasma corticosterone levels were significantly higher for the isolated-60 condition compared to the no-test and social-60 groups, $p<0.005$. To determine the effects of varying lengths of isolation on plasma corticosterone, a one-way ANOVA was conducted on data across the isolated groups. This analyses revealed a significant main effect for Time, $F(5,29)=3.512$, $p<0.05$. Post Hoc analyses demonstrated that mean plasma corticosterone levels were significantly higher for the 10 and 15 minute groups compared to the 5, 40, and 60 minute groups, $p^s<0.05$.

To examine the relationship between plasma corticosterone response and DVocs under increasing lengths of social separation, it was first necessary to convert DVocs to a rate/minute function (i.e., cumulative DVoc/isolation length). As is evident in FIG. 4, a positive relationship existed between plasma corticosterone levels and rate of distress vocalizations. A correlational analyses of these data yielded a significant effect ($r=0.59$, $p<0.0001$).

Distress vocalizations in the social-60 condition averaged below 50 DVocs/5 minute block and remained stable throughout the test session (see FIG. 2). In chicks isolated for 60 minutes, distress vocalizations were approximately 350 vocalizations in the first five minute block, gradually declined over the 10-15 minute, and then stabilized between 200 and 250 DVocs/5 minute block throughout the remaining portion of the testing session. All other isolated groups demonstrated this behavioral trend, a pattern of which is indicative of learned helplessness. These results are consistent with that of Example 1 and demonstrate that the pattern of DVocs in isolated chicks is clearly characterized by three components: initial protest, behavioral despair and learned helplessness.

The no-test and social groups displayed essentially identical plasma corticosterone levels (11.29 and 11.13 respectively), indicating that the "low stress" (i.e. social) testing procedure does not elevate plasma corticosterone. However, isolation from social companions produced a marked elevation in plasma corticosterone. This finding is consistent with other studies demonstrating that plasma corticosterone is elevated in response to various external stressors, such as exposure to a predator, food deprivation, social separation, 24 hour illumination, and loud noises (C. Cook. *Stress Induces CRF Release in the Paraventricular Nucleus, and Both CRF and BAGA Release in the Amygdala*, 84(4) Physiol. and Behavior 751-62 (2004); P. Willner. *Validity, Reliability, and Utility of the Chronic Mild Stress Model of Depression: A 10-Year Review and Evaluation*, 134(4) Psychopharma. 319-29 (1997)). Plasma corticosterone was elevated for all of the isolated conditions. The increase in plasma corticosterone is most prominent for the isolated-10 and isolated-15 conditions. Plasma corticosterone levels declined for the isolated-20, -40, -60 conditions, but remained elevated in comparison to chicks tested in the social condition (See FIG. 3). Similar patterns of corticosterone responses (i.e., initial elevation and subsequent decline) have been found in rats subjected to maternal separation (P. M. Plotsky et al. *Central and Feedback Regulation of Hypothalamic Corticotrophin-Releasing Factor Secretion*, 172 Cibia Foundation Symposium. 59-84 (1993)) and is consistent with reports that corticosterone produces negative feedback on HPA axis activity (R. M. Sapolsky. *Glucocorticoid Feedback Inhibition of Adrenocorticotropic Hormone Secretagogue Release*, 51 Neuroendocrin. 328-36 (1990)).

Figure 4:
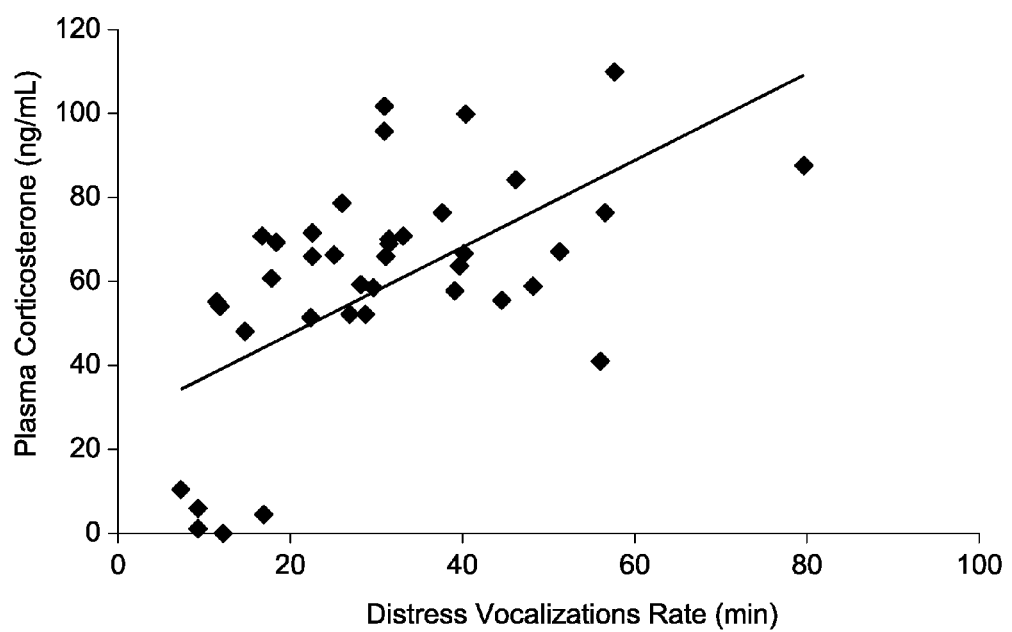
FIG. 4 shows the relationship between corticosterone levels (ng/mL) and distress vocalizations in all groups. (r=0.59, p<0.0001).

As is evident in FIG. 4, a positive relationship exists between distress vocalizations and plasma corticosterone levels in chicks, one of which higher levels of plasma corticosterone correspond to higher distress vocalizations in isolated chicks. This finding is consistent with previous work in this lab that shows that a positive relationship (r=0.49) exists between corticosterone and distress vocalizations (M. W. Feltenstein et al. Physiol. Behav. 2003, supra). Whether corticosterone levels directly alter rates of distress vocalizations was not addressed in the experiment.

Previous research in young domestic fowl has demonstrated that isolation from social companions for up to two hours produces a pattern of DVocs that (E. Lehr 1989, supra) describes as a state akin to learned helplessness, a common symptom of depression that arises in response to an uncontrollable stressor and is associated with a loss of motivated behavior. According to Lehr, chicks exhibited an initial "protest" and subsequent "resignation" (i.e. learned helplessness) over the test session. However, Lehr provided no actual time-course data to characterize this pattern of behavior and uses cumulative DVocs for the two hr session as the measure of learned helplessness. I believe that Lehr's study conflates a model of anxiety with a model of depression.

Indeed, a time course analysis of DVocs and the differential efficacy of chlordiazepoxide and imipramine on the pattern of distress calls demonstrate that both anxiety and depression can effectively be modeled in chicks (see FIG. 1). In this invention, DVocs are maximal at the first five minute of the test session and marks the initial protest or the anxiety phase of the model. This is followed by a transitional phase I label behavioral despair and it is characterized by the notable decrease in DVocs during the next 10-15 minute of social separation. The final phase begins at about the 20 minute block and marks the beginning of the learned helplessness or depression phase of the model. This latter phase is characterized by reduced and stable pattern of DVocs for the remainder of the test session. I believe it is unnecessary to subject animals to the entire 1-2 hr test session to effectively model depression. In fact, my laboratory was capable of detecting imipramine's antidepressant effects in as little as five minute of DVoc sampling and as early as the 20 minute time block. While longer test sessions (e.g., up to 40 or 60 minute) do effectively capture the depression component and likely reduce variability it would be at the expense of model utility.

Isolation from social companions is a potent stressor in young domestic fowl and leads to increased activity of the HPA axis and elevated corticosterone levels. Corticosterone levels showed a peak response at 10-15 minute into the test session and gradually declined thereafter. It is interesting to note that corticosterone negative feedback in regulating activity of the HPA axis is largely dependent on the nature of the stressor. Research suggests that emotional stressors produce a greater negative feedback on the HPA axis activity than do physical stressors (P. M. Plotsky et al. 1993, supra at). In the present experiment, the pattern of corticosterone response (i.e., the decline beyond 15 minute) indicates that social separation is an emotional stressor in the young domestic fowl and, thus, provides additional convergent validity of the paradigm as an anxiety/depression model.

Collectively, the behavioral, pharmacological and neuroendocrine data shown in Example 1 & 2 show that the present invention is a paradigm capable of screening compounds for anxiolytic and/or antidepressant activity. The advantages of the present invention over rodent-based depression models such as the Porsolt-forced swim test and the tail suspension test are numerous. Using the criteria outlined by P. Willner in Behavioural Models in Psychopharmacology: Theoretical, Industrial and Clinical Perspectives (Willner P. (ed.) pp. 3-18 (Cambridge University Press, Cambridge, 1991)) this assay possesses high utility and high-throughput as it 1) uses a low-cost animal ($0.50 a chick; (J. T. Roach et al. *Characterization Of The Chick Carrageenan Response*, 994 Brain Research 216-25 (2003)), 2) tests at a young age, 3) employs one relatively short test session (20-30 minute), 4) measures a species-typical response that is easily recorded, 5) screens for two drug properties in a single test and 6) requires simple statistical analyses. Furthermore, the present invention is unique in that it meets the NIH's 3R policy to Reduce, Refine, and Replace animals in research (Office of Laboratory Animal Welfare, 2002). The model reduces the number of purpose-bred research animals as male chicks are a by-product of the commercial egg-laying industry (i.e., cockerels are discarded at hatch; J. T. Roach & K. J. Sufka, Id.) Also, the model possesses a refined methodology as it minimizes the stress-provoking stimuli to a single; relatively short (20-30 minute) test session. And finally, the model replaces the standard rodent-based models of anxiety with a phylogentically lower and less sentient species.

EXAMPLE 3

5 Day Drug Probe Studies

Subjects and Housing Procedures. Cockerels (*Gallus gallus*; W36; Cal-Maine Foods, Inc.; Mendenhall, Miss.) were received one-day posthatch and housed in 34×57×40 cm stainless steel cages with 12-13 chicks per cage. Food (Purina Start and Grow, St. Louis, Mo.) and water were available ad libitum through one quart gravity-fed feeders (Murray MacMurray; Model 4BGFJ) and waterers (Murray MacMurray; Model 4YQW0). Room temperature was maintained at 29±1° C. and overhead illumination was maintained on a 12 hr light-dark cycle. Daily maintenance, which was conducted during the first three hr of the light cycle, involved refilling the waterer, refilling the feeder, and replacement of tray liners.

Apparatus. The testing apparatus consisted of a six-unit test apparatus containing Plexiglas viewing chambers (25×25×22 cm) placed in sound-attenuating enclosures. Each unit was illuminated and heated by a 25-W light bulb. Ventilation was provided by an eight centimeter diameter rotary fan (Commonwealth Model FP-108AX 51). Miniature video cameras (SuperCircuit Model PC60XP) mounted in the sound-attenuating enclosures at floor level and routed through a Multiplexor (SuperCircuit Model PC47MC) provided televised display of the chicks for behavioral observation. Distress vocalizations (DVocs) were recorded by microphones (Lafayette Instruments Model 3-675-001) mounted in the ceilings of the Plexiglas chambers and connected to digital sound-activating relays (Lafayette Instruments Model 63040A; settings: 75% sensitivity and 0.10 s delay) that triggered electromechanical counters (Lafayette Instruments Model 58004).

Drugs. For the drug probes, either vehicle (0.9% physiological saline or DMSO) or the following drugs with established clinical efficacy for anxiety and/or depression were used in the experiments: chlordiazepoxide, 2.5, 5.0, 10.0, 15.0 mg/kg; clonidine, 0.10, 0.15, 0.20, 0.25 mg/kg; imipramine, 1, 3, 10, 15 mg/kg; maprotiline, 2.5, 5.0, 10.0, 20.0 mg/kg; fluoxetine, 1, 5, 10, 15 mg/kg.

Drug Probes. All experiments were conducted between five- and seven days posthatch. The groups in each experiment formed a 1×5 factorial design with a hanging control condition (n=9-12). The two vehicle control groups constituted the social separation stress manipulation. This manipulation involved placing a chick in the Plexiglas test chamber either in isolation or with two social companions for a 120 min test observation period. All drug probes were tested in the isolation condition.

Vehicle or a drug was administered IM fifteen minutes prior to testing. Dependent measures that were collected during the test session were DVocs to index separation stress and sleep onset latency (SOL) to index sedation. DVocs were defined as the vocalizations that are picked up by the electromechanical counters. SOL was defined as the time in which a chick adopts a sleep-like posture with either its chest in full contact with the floor and its eyes closed or its legs in a wide posture, its head drooping, and its eyes closed. Following each six-chick test session, the animals were returned to their home cage. After all animals were tested, they were euthanized via $CO^2$ asphyxiation.

Figure 5:
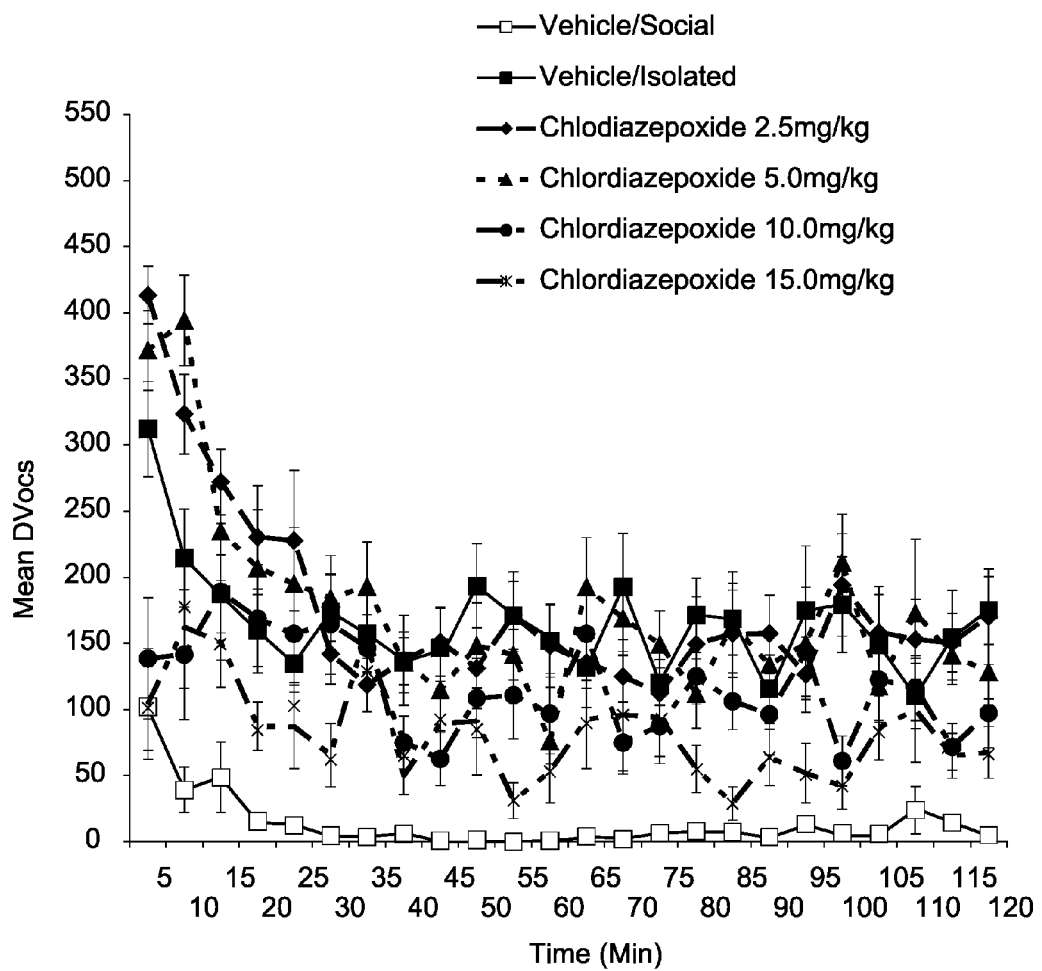
FIG. 5 shows the effects of chlordiazepoxide on isolation-induced DVocs across the 2 hr test session. Values represent mean (±SEM) DVoc for each 5 min time block. Chlordiazepoxide effects on the anxiety-like and depressive like phases of the test session are detailed in FIG. 6.
Figure 6A:
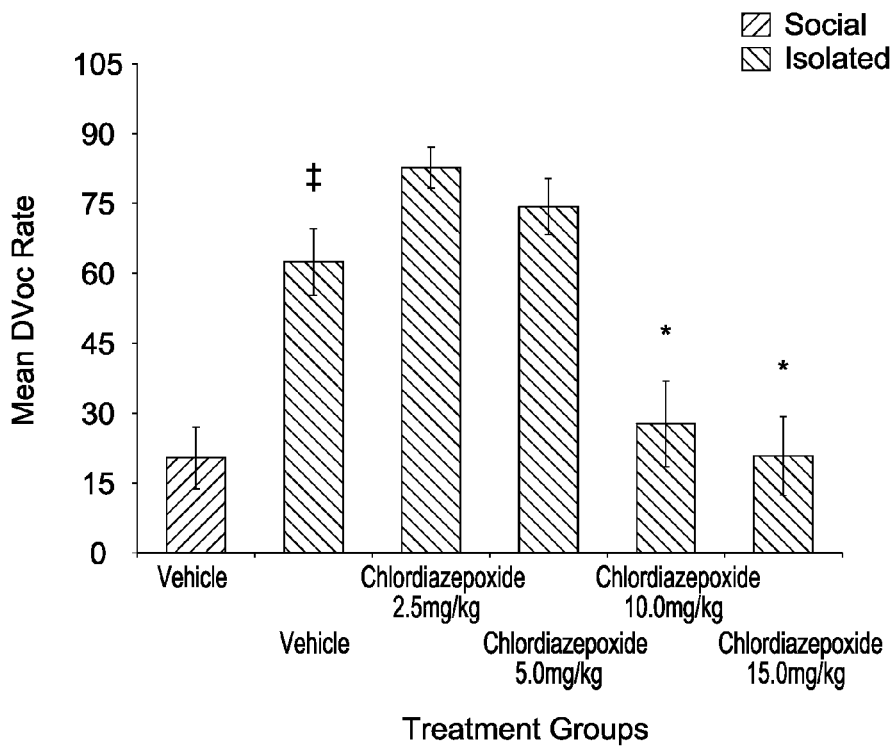
FIG. 6A highlights the effects of chlordiazepoxide on the isolation-induced DVoc rate during the anxiety phase of the isolation test session (0-5 min). Values represent mean (±SEM) DVoc. ‡ indicates significant increase in DVoc rate (stress effect) compared to the vehicle/social condition. * indicates a significant attenuation of DVocs (anxiolytic effect) compared to the vehicle/isolated condition.
Figure 6B:
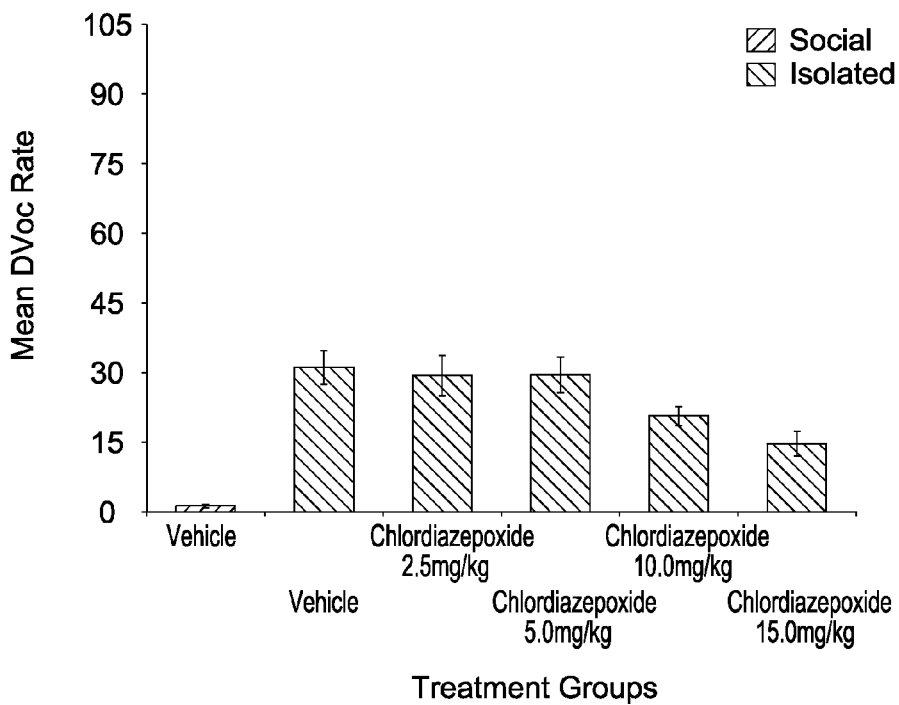
FIG. 6B highlights the effects of chlordiazepoxide on the isolation-induced DVoc rate during the depression phase of the isolation test session (30-120 min). Values represent mean (±SEM) DVoc rate. All $p^s<0.05$.

Chlordiazepoxide. The effects of social separation and chlordiazepoxide on DVocs across the test session are summarized in FIG. 5, while the effects of these factors on DVoc rates in the anxiety-like phase and the depression-like phase are summarized in FIGS. 6A and 6B. The two highest doses of chlordiazepoxide (10 mg/kg and 15 mg/kg) attenuated DVocs during the test session, most notably in the first five min time block (i.e., the anxiety-like phase), while none of the doses exacerbated DVocs during the test session. Consistent with these descriptions, at the five min time block a one-way ANOVA of the isolated groups revealed a significant effect [$F(4, 56)=15.173$, $p<0.0001$]. Post hoc analyses showed a significant attenuation of the separation-induced DVoc rate at the 10 mg/kg and 15 mg/kg doses ($p^s<0.005$). A one-way ANOVA of the isolated groups during the depression-like phase (30-120 min) revealed a significant effect [$F(4, 56)=4.341$, $p<0.005$]. Post hoc analyses demonstrated a significant attenuation of the DVoc rate in the 10 mg/kg and 15 mg/kg doses ($p^s<0.025$).

Chicks receiving the 10 mg/kg dose had a lower SOL compared to vehicle/isolated chicks. Consistent with this description, a one-way ANOVA revealed a marginally significant effect [$F(4, 56)=2.268$, $p=0.074$]. Post hoc analyses demonstrated a significant SOL reduction in the 10 mg/kg dose ($p<0.05$).

Figure 7:
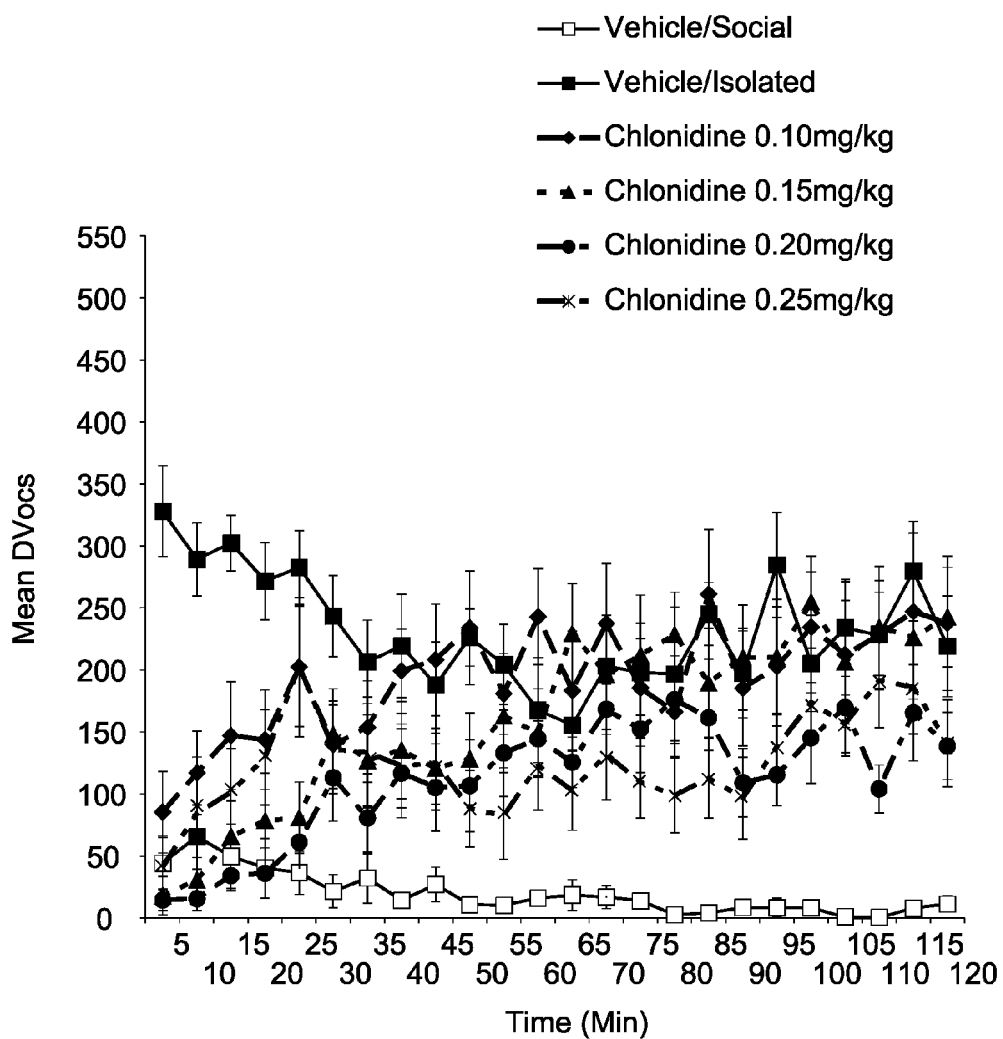
FIG. 7 shows the effects of clonidine on isolation-induced DVocs across the 2 hr test session. Values represent mean (±SEM) DVoc for each 5 min time block. Clonidine effects on the anxiety-like and depressive like phases of the test session are detailed in FIG. 8.
Figure 8A:
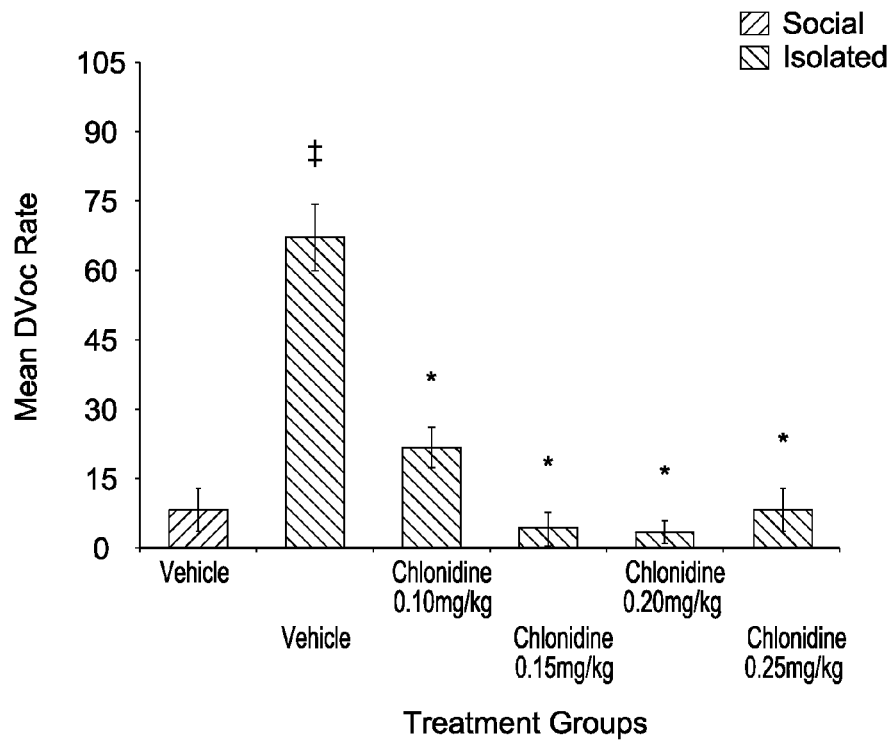
FIG. 8A highlights the effects of clonidine on the isolation-induced DVoc rate during the anxiety phase of the isolation test session (0-5 min). Values represent mean (±SEM) DVoc. ‡ indicates significant increase in DVoc rate (stress effect) compared to the vehicle/social condition. * indicates a significant attenuation of DVocs (anxiolytic effect) compared to the vehicle/isolated condition.
Figure 8B:
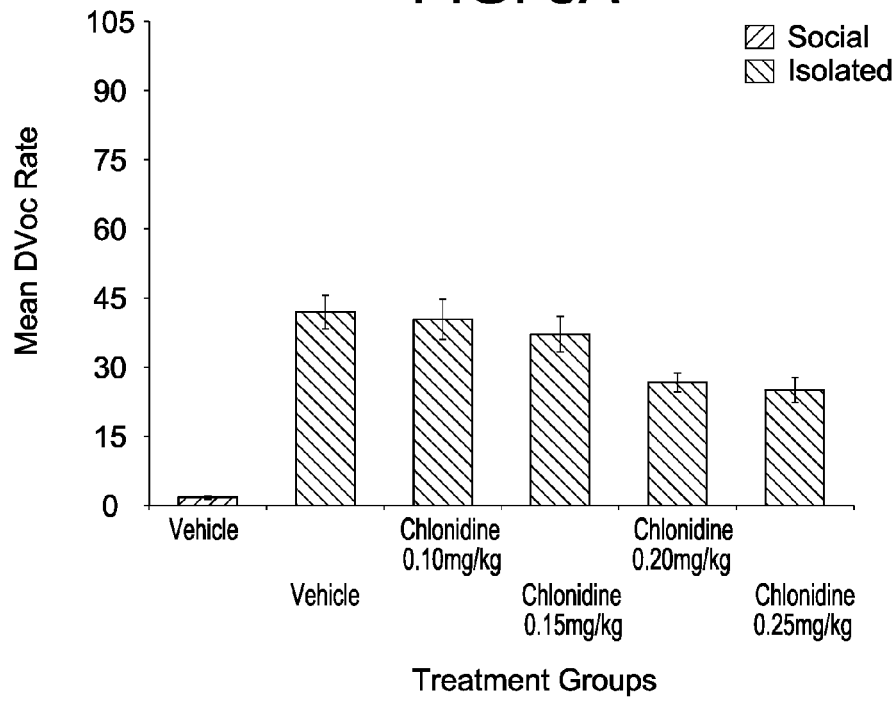
FIG. 8B highlights the effects of clonidine on the isolation-induced DVoc rate during the depression phase of the isolation test session (30-120 min). Values represent mean (±SEM) DVoc rate. All $p^s<0.05$.

Clonidine. The effects of social separation and clonidine on DVocs across the test session are summarized in FIG. 7, while the effects of these factors on DVoc rates in the anxiety-like phase and the depression-like phase are summarized in FIGS. 8A and 8B. All doses of clonidine attenuated DVocs during the first five min time block (i.e., the anxiety-like phase), while none of the doses exacerbated DVocs during the test session. Consistent with these descriptions, a one-way ANOVA of the isolated groups revealed a significant effect at the five min time block [$F(4, 56)=26.030$, $p<0.0001$]. Post hoc analyses showed a significant attenuation of the separation-induced DVoc rate at all doses ($p^s<0.0001$). A one-way ANOVA of the isolated groups during the depression-like phase (30-120 min) did not reveal a significant effect.

Chicks receiving the 0.15 mg/kg, 0.20 mg/kg and 0.25 mg/kg doses had a lower SOL compared to vehicle/isolated chicks. Consistent with this description, a one-way ANOVA revealed a significant effect [$F(4, 56)=2.789$, $p<0.05$]. Post hoc analyses demonstrated a significant SOL reduction in the 0.15 mg/kg and 0.20 mg/kg doses ($p^s<0.05$) and a marginally significant reduction in the 0.25 mg/kg dose ($p=0.085$).

Figure 9:
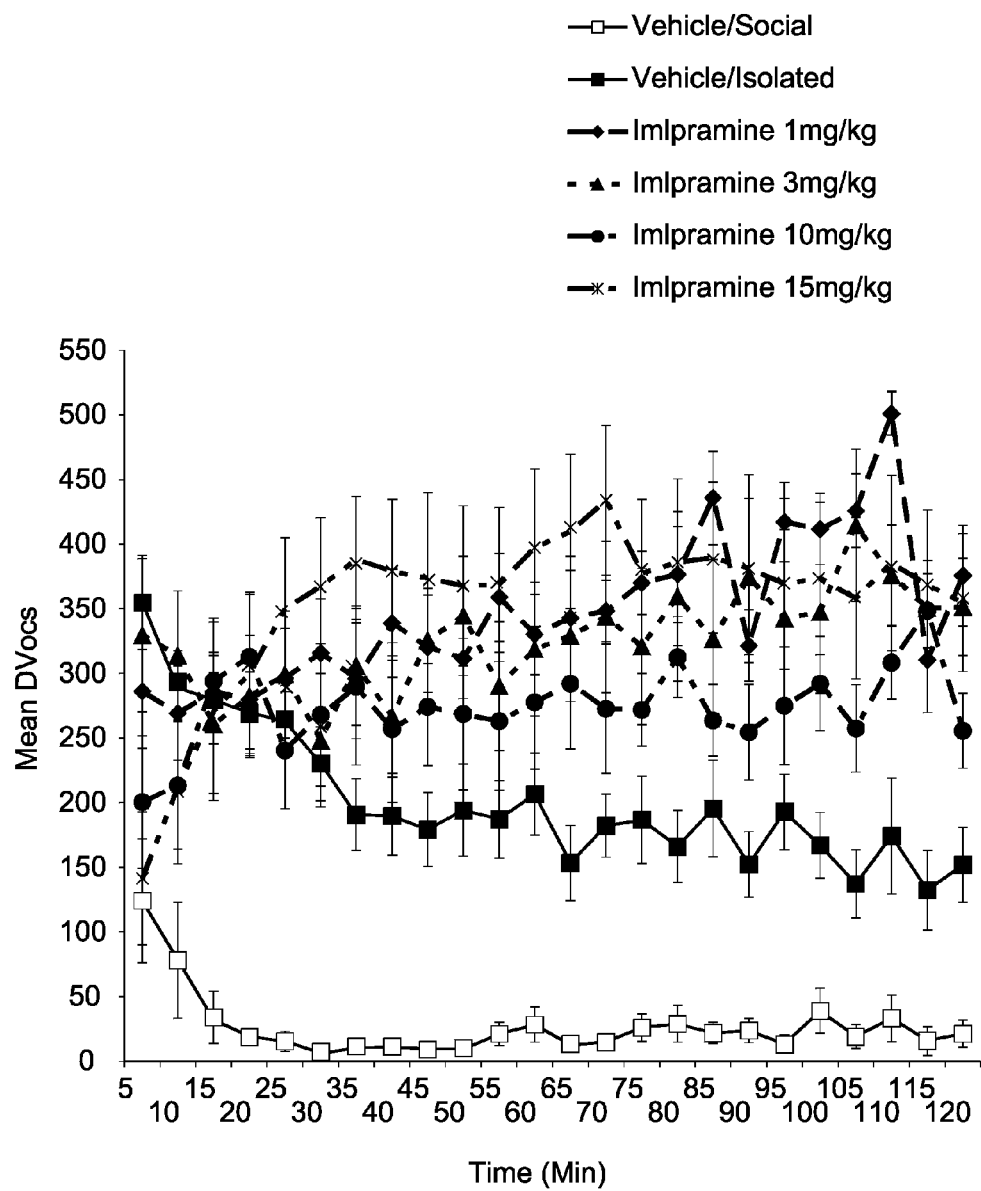
FIG. 9 shows the effects of imipramine on isolation-induced DVocs across the 2 hr test session. Values represent mean (±SEM) DVoc for each 5 min time block. Imipramine effects on the anxiety-like and depressive like phases of the test session are detailed in FIG. 10.
Figure 10A:
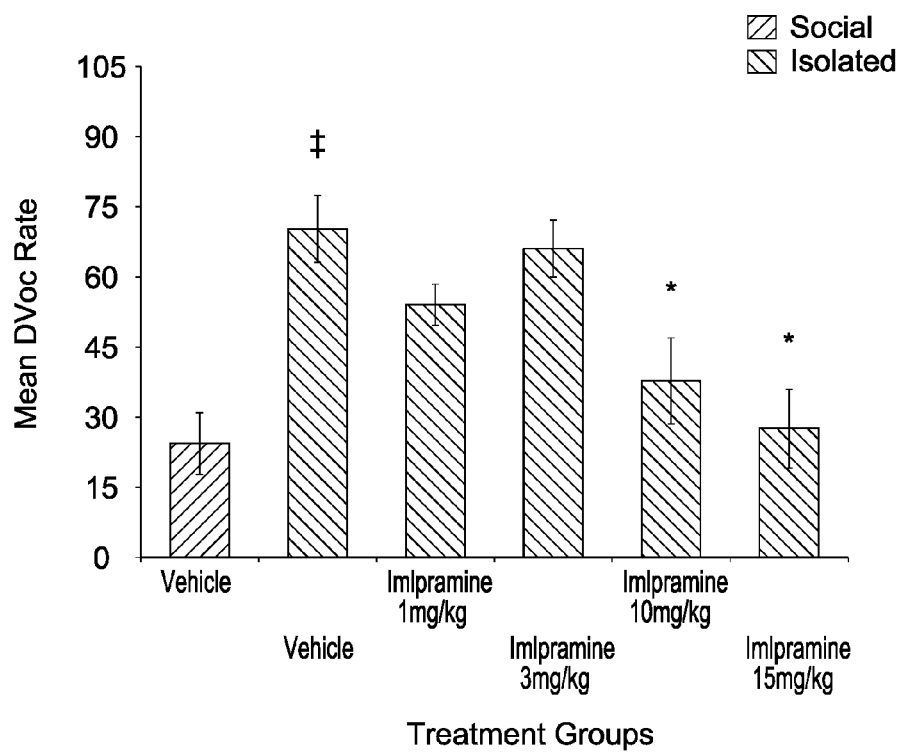
FIG. 10A highlights the effects of imipramine on the isolation-induced DVoc rate during the anxiety phase of the isolation test session (0-5 min). Values represent mean (±SEM) DVoc. ‡ indicates significant increase in DVoc rate (stress effect) compared to the vehicle/social condition. * indicates a significant attenuation of DVocs (anxiolytic effect) compared to the vehicle/isolated condition.
Figure 10B:
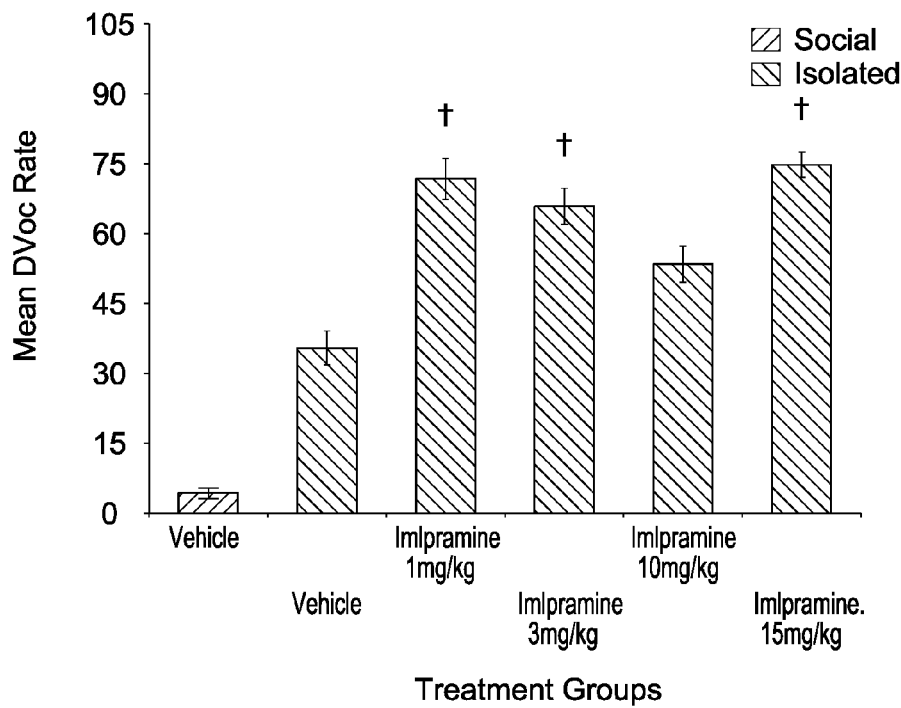
FIG. 10B highlights the effects of imipramine on the isolation-induced DVoc rate during the depression phase of the isolation test session (30-120 min). Values represent mean (±SEM) DVoc rate. † indicates a significant increase of DVocs (antidepressant effect) compared to the vehicle/isolated condition. All $p^s<0.05$.

Imipramine. The effects of social separation and imipramine on DVocs across the test session are summarized in FIG. 9, while the effects of these factors on DVoc rates in the anxiety-like phase and the depression-like phase are summarized in FIGS. 10A and 10B. The two highest doses of imipramine (10 mg/kg and 15 mg/kg) attenuated DVocs during the anxiety-like phase of the test session (i.e., the first five min time block) and all of the doses exacerbated DVocs during the depression-like phase of the test session (i.e., the 30-120 min time block). Consistent with these descriptions, a one-way ANOVA of the isolated groups revealed a significant effect at the five min time block [$F(4, 52)=3.456$, $p<0.025$]. Post hoc analyses showed a significant attenuation of the separation-induced DVoc rate at the 10 mg/kg and 15 mg/kg doses ($p^s<0.05$). A one-way ANOVA of the isolated groups during the depression-like phase (30-120 min) revealed a significant effect [$F(4, 52)=5.044$, $p<0.005$]. Post hoc analyses demonstrated a significant exacerbation of the DVoc rate in the 1 mg/kg, 3 mg/kg and 15 mg/kg doses ($p^s<0.005$) and a marginally significant exacerbation in the 10 mg/kg dose condition ($p=0.058$).

Figure 11:
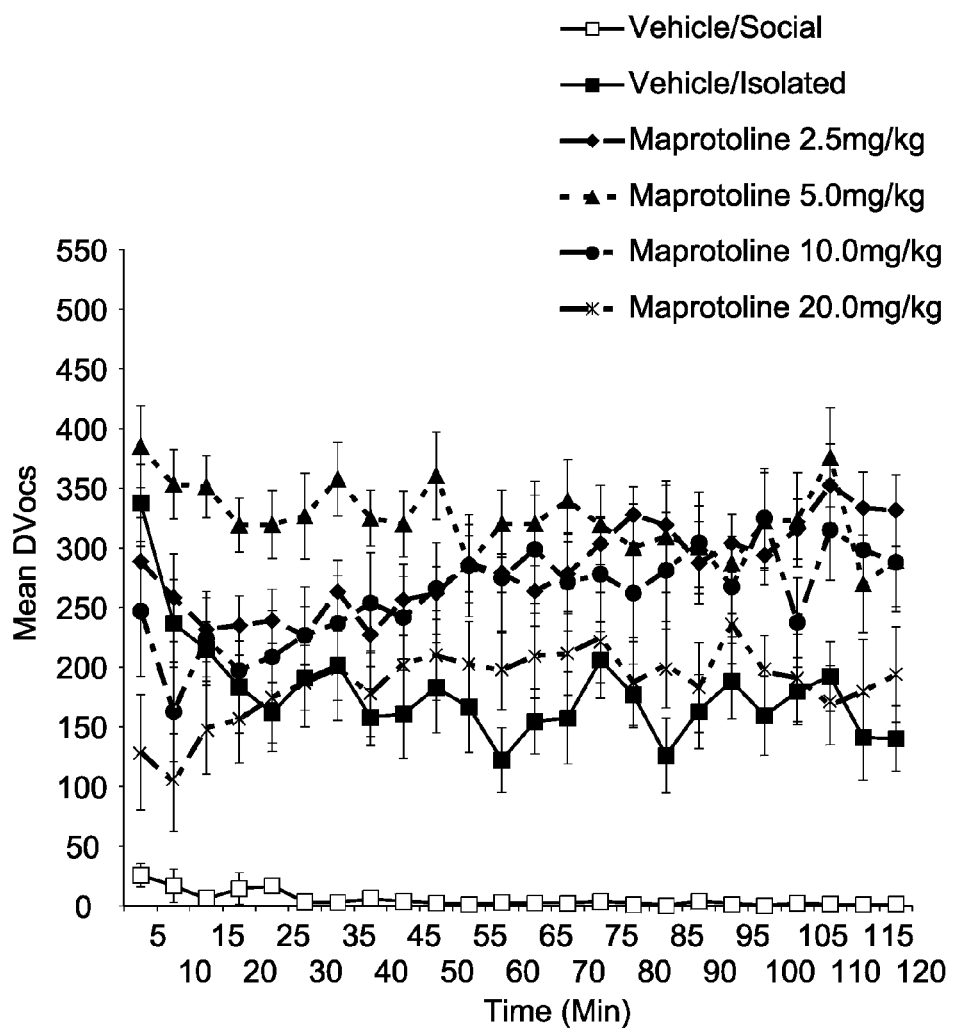
FIG. 11 shows the effects of maprotiline on isolation-induced DVocs across the 2 hr test session. Values represent mean (±SEM) DVoc for each 5 min time block. Maprotiline effects on the anxiety-like and depressive like phases of the test session are detailed in FIG. 12.
Figure 12A:
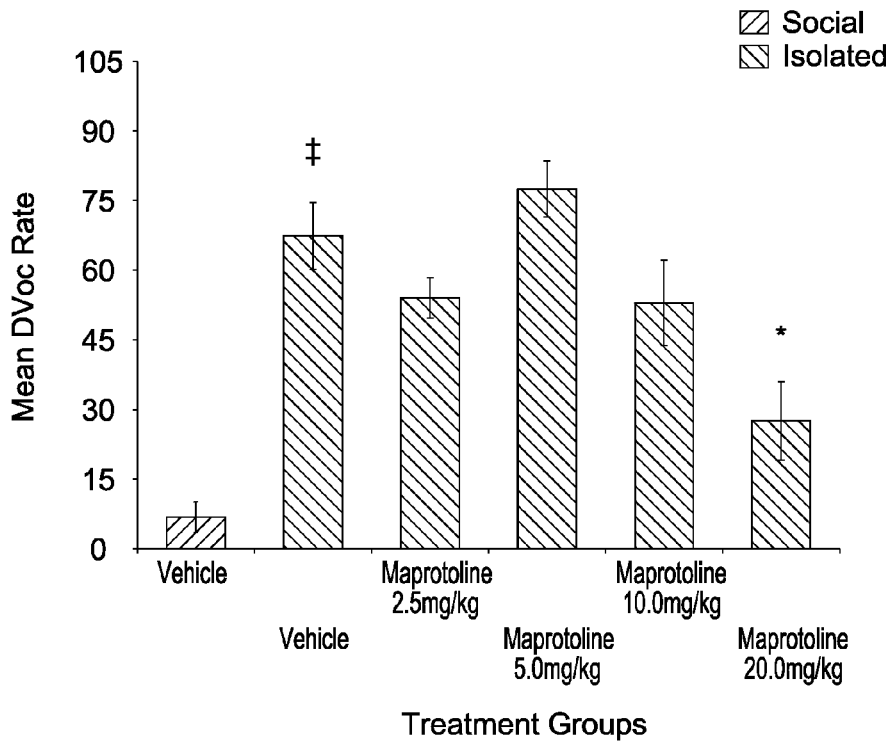
FIG. 12A highlights the effects of maprotiline on the isolation-induced DVoc rate during the anxiety phase of the isolation test session (0-5 min). Values represent mean (±SEM) DVoc. ‡ indicates significant increase in DVoc rate (stress effect) compared to the vehicle/social condition. * indicates a significant attenuation of DVocs (anxiolytic effect) compared to the vehicle/isolated condition.
Figure 12B:
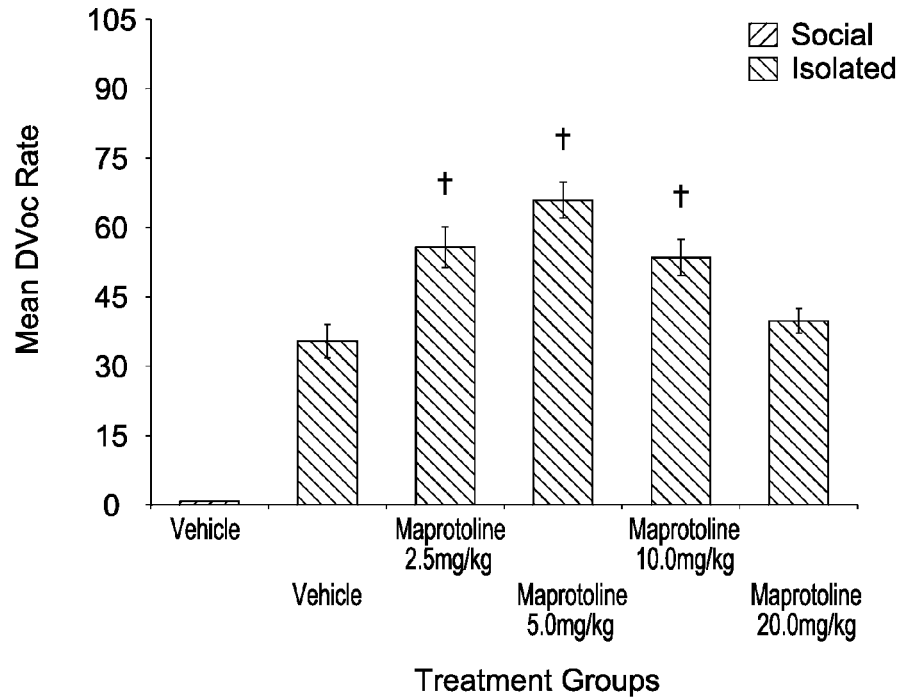
FIG. 12B highlights the effects of maprotiline on the isolation-induced DVoc rate during the depression phase of the isolation test session (30-120 min). Values represent mean (±SEM) DVoc rate. † indicates a significant increase of DVocs (antidepressant effect) compared to the vehicle/isolated condition. All $p^s<0.05$.

Maprotiline. The effects of social separation and maprotiline on DVocs across the test session are summarized in FIG. 11, while the effects of these factors on DVoc rates in the anxiety-like phase and the depression-like phase are summarized in FIGS. 12A and 12B. The highest dose of maprotiline (20 mg/kg) attenuated DVocs during the anxiety-like phase of the test session (i.e., the first five min time block), while the three lowest doses (2.5 mg/kg, 5 mg/kg, and 10 mg/kg) exacerbated DVocs during the depression-like phase of the test session (i.e., 30-120 min time blocks). Consistent with these descriptions, a one-way ANOVA of the isolated groups revealed a significant effect at the five min time block [$F(4, 59)=5.384$, $p<0.0001$]. Post hoc analyses showed a significant attenuation of the separation-induced DVoc rate at the 20 mg/kg dose (p<0.005). A one-way ANOVA of the isolated groups during the depression-like phase (30-120 min) revealed a significant effect [$F(4, 59)=4.872$, $p<0.005$]. Post hoc analyses demonstrated a significant exacerbation of the DVoc rate in the 1 mg/kg, 3 mg/kg and 15 mg/kg doses ($p^s<0.01$).

Figure 13:
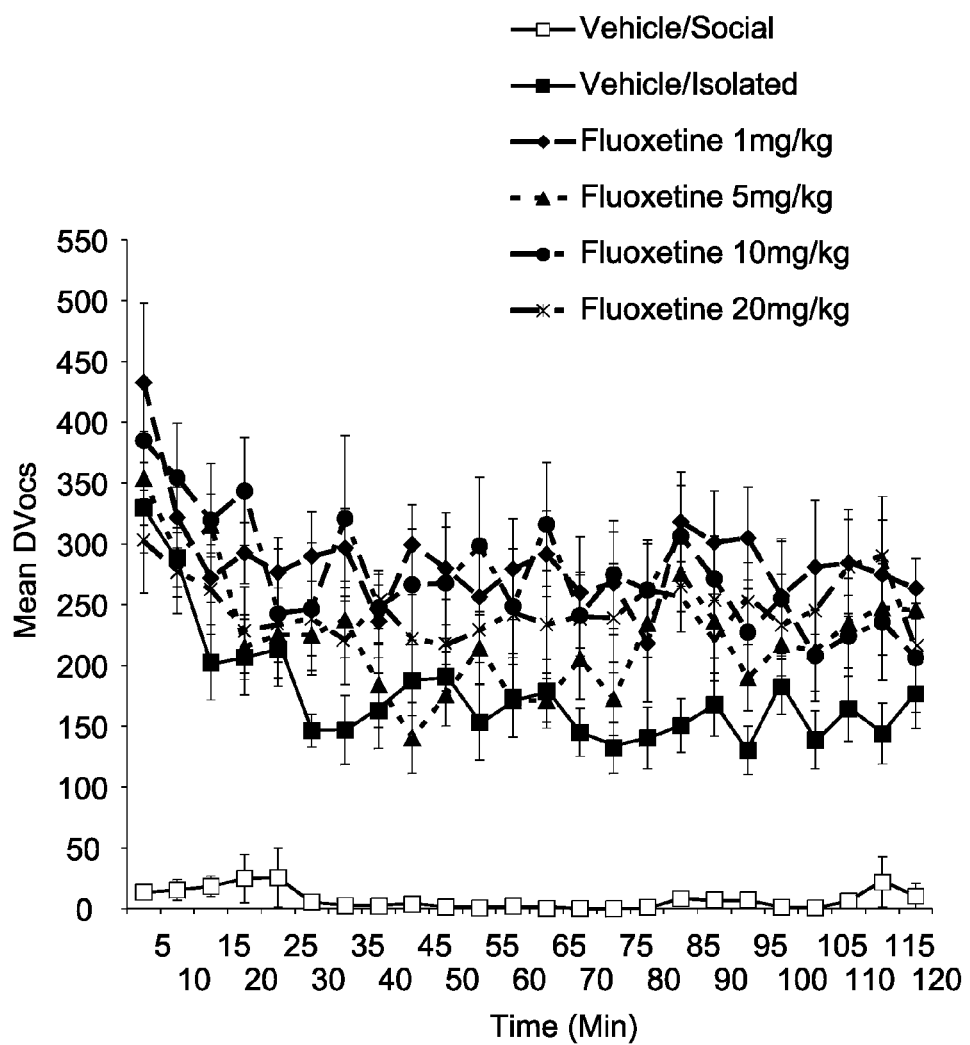
FIG. 13 shows the effects of fluoxetine on isolation-induced DVocs across the 2 hr test session. Values represent mean (±SEM) DVoc for each 5 min time block. Fluoxetine effects on the anxiety-like and depressive like phases of the test session are detailed in FIG. 14.
Figure 14A:
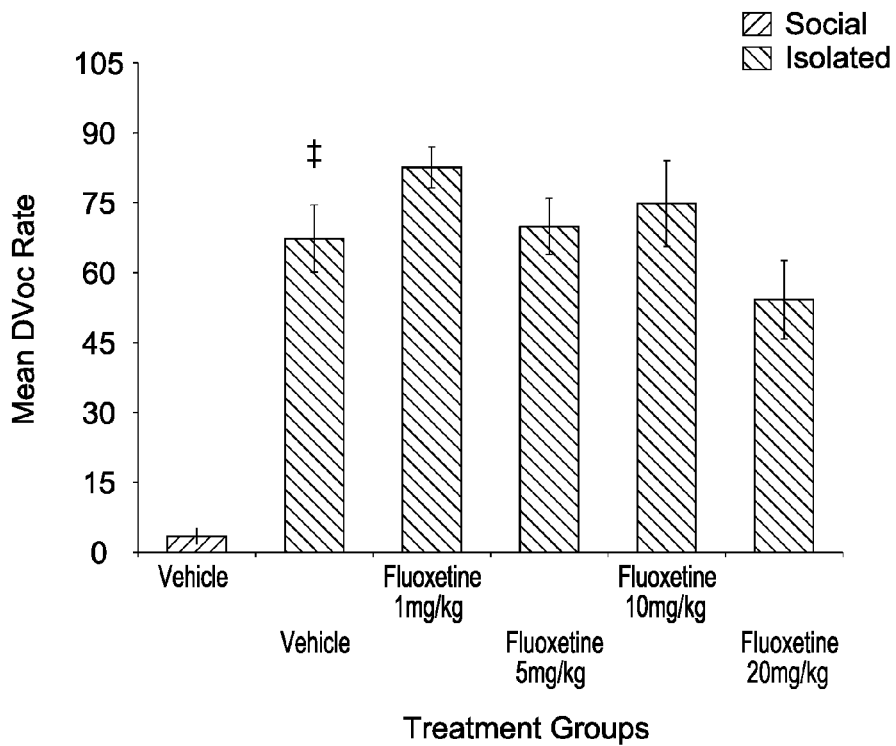
FIG. 14A highlights the effects of fluoxetine on the isolation-induced DVoc rate during the anxiety phase of the isolation test session (0-5 min). Values represent mean (±SEM) DVoc. ‡ indicates significant increase in DVoc rate (stress effect) compared to the vehicle/social condition.
Figure 14B:
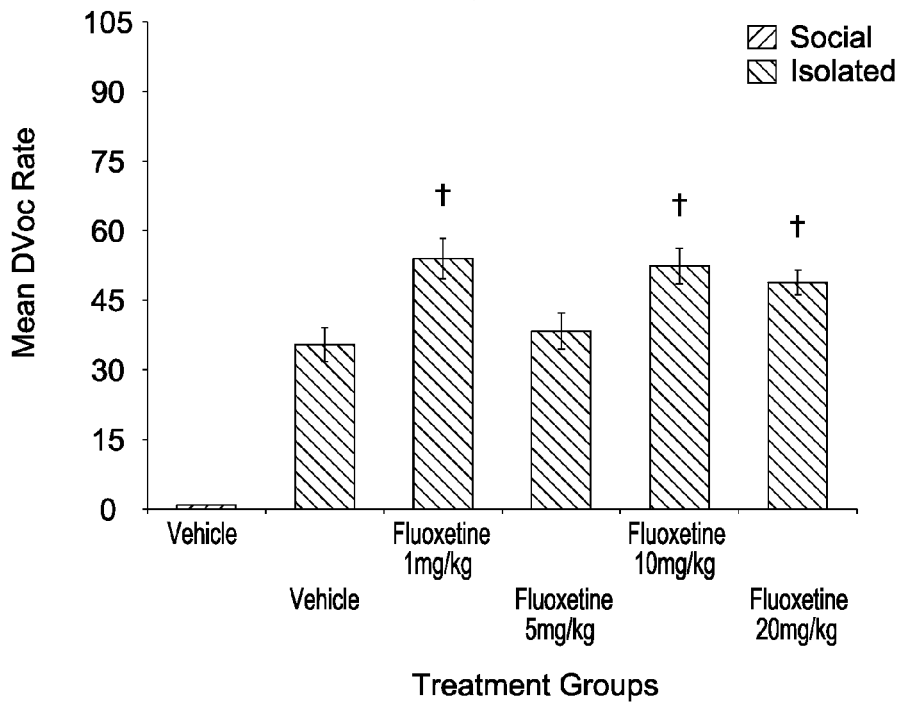
FIG. 14B highlights the effects of fluoxetine on the isolation-induced DVoc rate during the depression phase of the isolation test session (30-120 min). Values represent mean (±SEM) DVoc rate. † indicates a significant increase of DVocs (antidepressant effect) compared to the vehicle/isolated condition. All $p^s<0.05$.

Fluoxetine. The effects of social separation and fluoxetine on DVocs across the test session are summarized in FIG. 13, while the effects of these factors on DVoc rates in the anxiety-like phase and the depression-like phase are summarized in FIGS. 14A and 14B. While none of the doses of fluoxetine attenuated DVocs during the anxiety-like phase of the test session (i.e., the first five min time block), the 1 mg/kg, 10 mg/kg, and 20 mg/kg doses exacerbated DVocs during the depression-like phase of the test session (i.e., 30-120 min time blocks). Consistent with these descriptions, a one-way ANOVA of the isolated groups did not reveal a significant effect at the five min time block. A one-way ANOVA of the isolated groups during the depression-like phase (30-120 min) revealed a significant effect [$F(4, 54)=2.797$, $p<0.05$]. Post hoc analyses demonstrated a significant exacerbation of the DVoc rate in the 1 mg/kg, 10 mg/kg and 20 mg/kg doses ($p^s<0.05$).

EXAMPLE 4

IL-6 Assay

Subjects and Housing Procedures. Cockerels (*Gallus gallus*; W36; Cal-Maine Foods, Inc.; Mendenhall, Miss.) were received one-day posthatch and housed in 34×57×40 cm stainless steel cages with 12-13 chicks per cage. Food (Purina Start and Grow, St. Louis, Mo.) and water were available ad libitum through one quart gravity-fed feeders (Murray MacMurray; Model 4BGFJ) and waterers (Murray MacMurray; Model 4YQW0). Room temperature was maintained at 29±1° C. and overhead illumination was maintained on a 12 hr light-dark cycle. Daily maintenance, which was conducted during the first three hr of the light cycle, involved refilling the waterer, refilling the feeder, and replacement of tray liners.

Apparatus. The testing apparatus consisted of a six-unit test apparatus containing Plexiglas viewing chambers (25×25×22 cm) placed in sound-attenuating enclosures. Each unit was illuminated and heated by a 25-W light bulb. Ventilation was provided by an eight centimeter diameter rotary fan (Commonwealth Model FP-108AX 51). Miniature video cameras (SuperCircuit Model PC60XP) mounted in the sound-attenuating enclosures at floor level and routed through a Multiplexor (SuperCircuit Model PC47MC) provided televised display of the chicks for behavioral observation. Distress vocalizations (DVocs) were recorded by microphones (Lafayette Instruments Model 3-675-001) mounted in the ceilings of the Plexiglas chambers and connected to digital sound-activating relays (Lafayette Instruments Model 63040A; settings: 75% sensitivity and 0.10 s delay) that triggered electromechanical counters (Lafayette Instruments Model 58004).

The groups were tested for either 0, 15, 30, 60, or 120 minutes in isolation, or 120 min with social companions (n=6). Vehicle was administered IM fifteen minutes prior to testing. Following each test session, the animals were decapitated to allow for blood tissue collection. Blood samples were collected in EDTA tubes (BD Vacutainer $K_3$ EDTA) and immediately chilled on ice. Following the completion of the day's test session, blood was centrifuged for 15 min at 3000 rpm and plasma was removed. Plasma was stored at −80° C. until analysis. Plasma IL-6 concentrations were determined by an enzyme-linked immunosorbent assay (ELISA) kit (IL-6 Mouse EIA; ALPCO Diagnostics, Salem, N.H., USA). The assay was conducted according to the manufacturer's instructions. The intra-assay coefficient was 6.05%. For the IL-6 assay, only vehicle (0.9% physiological saline) was administered.

Statistical Analyses. In order to discretely analyze the drug effects in the anxiety-like state and the depression-like state, the raw DVoc data were converted to a rate per min score. The anxiety-like state DVoc rate consisted of the mean DVocs per min over the first five min of the test session. The depression-like state DVoc rate consisted of the mean DVocs per min from 30 min to 120 min. Following this conversion, the DVoc rates from the anxiety-like phase and depression-like phase were analyzed with a one-way ANOVA with Fisher's LSD post hoc analysis. Plasma IL-6 concentration data were analyzed using one-way ANOVA with Fisher's LSD post hoc analysis and independent sample t-tests.

Figure 15:
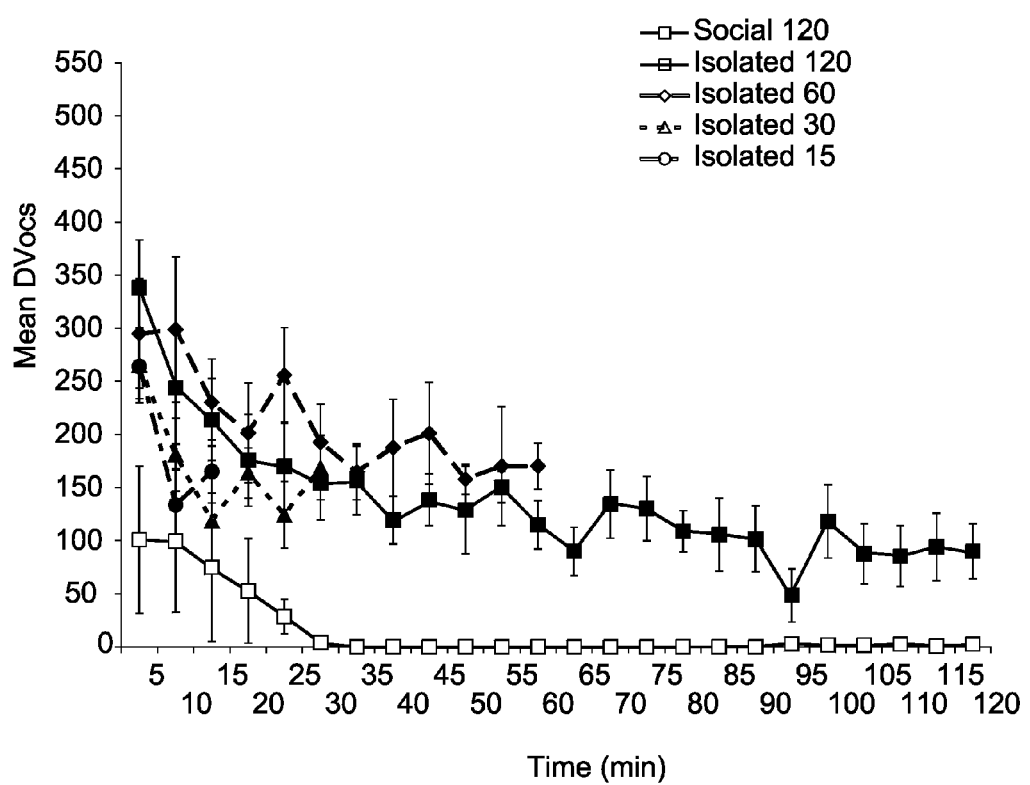
FIG. 15 shows the time course of isolation-induced DVocs across the 2 hr test session for chicks in the interleukin-6 study. Values represent mean (±SEM) DVoc for each 5 min time block.

The effects of social separation on DVocs for chicks tested for IL-6 are summarized in FIG. 15. In the two hour test session groups, the Isolated 120 group had a robust increase in DVocs compared to the Social 120 group. Consistent with this description, a between subjects ANOVA revealed significant main effect for Social Condition [$F(1, 10)=30.63$, $p<0.0001$] and a within subjects ANOVA revealed a significant main effect for Time [$F(23, 230)=5.99$, $p<0.0001$] and a non-significant Social Condition X Time interaction. In the Isolated 120 condition, the DVoc rates changed within the test session with the highest point occurring in the first five min time block (i.e., anxiety-like phase) followed by a decrease to 60% of that initial rate by the 15 min time block. DVoc rates stayed between 60% to 14% of the first five min block for the rest of the test session (i.e., depression-like phase). A repeated measures ANOVA conducted on the Isolated 120 group revealed a significant main effect [$F(23, 115)=4.95$, $p<0.0001$]. Paired samples t-tests showed significantly fewer DVocs for every time block (ten min-120 min) compared to the first five min time block (all $p^s<0.05$). All other Isolated conditions displayed a similar pattern with the DVoc rates changing within the test session, with the highest point occurring in the first five min time block (i.e., anxiety-like phase) followed by a decrease of that initial rate by the 15 min time block (all $p^S<0.05$).

Figure 16:
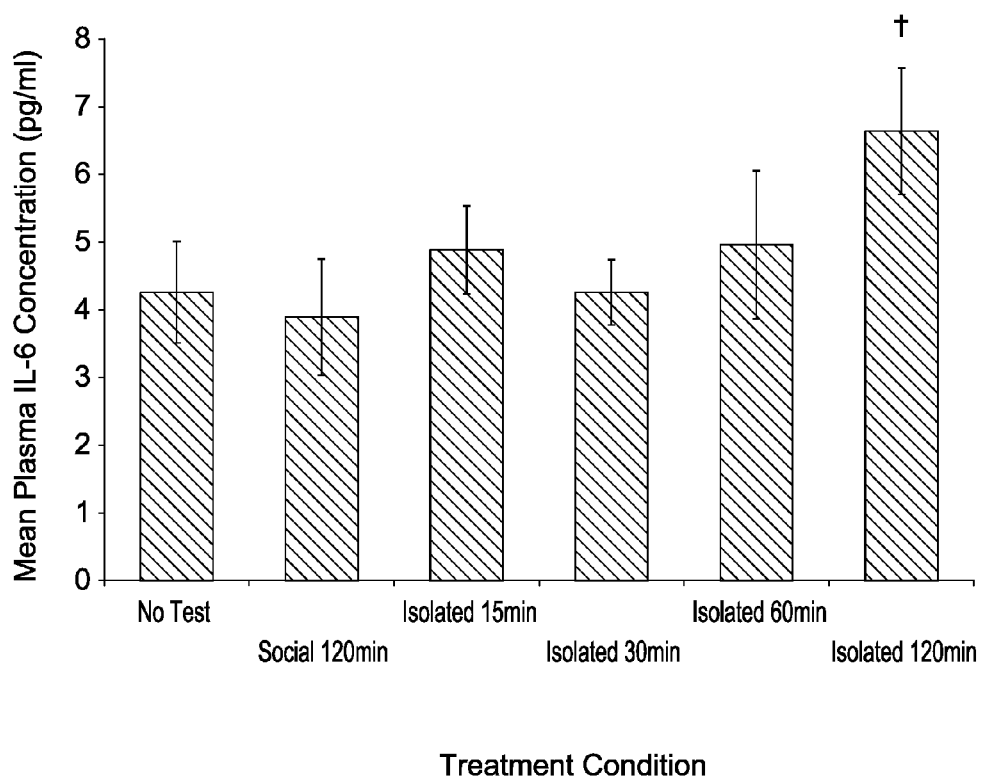
FIG. 16 shows the plasma concentration of interleukin-6 (pg/ml) across the 2 hr test session. Values represent mean (±SEM) concentration level. † indicates a marginally significant increase in plasma interleukin-6 concentration compared to the No-Test condition (p=0.067).

The effects of varying lengths of social separation on mean plasma IL-6 concentrations are summarized in FIG. 16. IL-6 levels were comparable between the No Test and the Social 120 min groups. The Isolated 120 group had IL-6 levels higher than either the No Test or Social 120 groups. All other Isolated groups had IL-6 levels between that of the Isolated 120, No Test and Social 120 groups. Consistent with this description, a one-way ANOVA of the No Test, Social 120 and Isolated 120 groups revealed marginally significant main effect [$F(2, 17)=3.06$, $p=0.077$]. Post hoc analyses show no significant difference between the No Test and Social 120 groups, a marginally significant difference between the No Test and Isolated 120 groups ($p=0.067$), and a significant difference between the Social 120 and Isolated 120 groups ($p<0.05$). A one-way ANOVA of the Isolated groups was not significant. Post hoc analyses reveal a marginally significant difference between the Isolated 120 and Isolated 30 groups ($p=0.055$).

EXAMPLE 5

Subjects and Housing Procedures. Cockerels (Production Red or Black Australorp, Ideal Poultry, Inc. Cameron, Tex., USA) were received 2 days posthatch and group housed in 34×57×40 cm cages at 12 chicks per cage. Food and water were available ad libitum. Daily maintenance included replacement of tray liners, re-filling food and replacing water. Lights were operated on a 12:12 light dark cycle. Supplemental heating sources provided housing temperatures at 32+/−1° C.

Apparatus. A six-unit testing apparatus containing Plexiglas chambers (25×25×22 cm) surrounded by sound attenuating media was used to record separation-induced vocalizations. Each unit was illuminated by a 25-W light bulb, and ventilated by an 8-cm-diameter rotary fan (Model FP-108AX 51, Commonwealth Industrial Corp., Taipei, Taiwan). Miniature video cameras (Model PC60XP, SuperCircuits, Inc., Liberty Hill, Tex., USA) mounted outside the observation chambers at floor level and routed through a multiplexor (Model PC47MC, SuperCircuits, Inc.) provided televised display of chicks for observation. Distress vocalizations (DVocs) were detected via microphones [Radio Shack Omnidirectional Model 33-3013 (modified for AC current)] mounted at the top of the Plexiglas chamber and routed to a computer equipped with custom designed software for data collection. DVocs were stored as a rate function in one-minute blocks on the hard drive and backed up onto a flash drive.

Procedure. At 5-6 days posthatch, chicks were removed from their home cage in squads of six and placed into an opaque plastic transport container. Body weight was determined for each chick for dosing and identification of outliers (i.e., low body weight). Chicks received a single IP injection of a drug probe or vehicle in a volume of 1 mL/kg. Following a 30 min injection-to-test interval, chicks were placed in isolation into the test apparatus for a 90 min test session. For the ketamine dose response studies, a group of non-isolated vehicle-treated chicks (one for each strain) were included as a control for the isolation manipulation. These non-isolated chicks were placed along with two conspecifics from separate cage into the observation chamber that contained mirrors positioned along the side-walls. Non-isolated chicks vocalize little if any throughout the test session but were included to highlight the robust social separation stress effect on DVocs. Being mindful to reduce the number of research animals when appropriate, this group was not included in the remaining dose response studies as vehicle isolated chicks served as the comparison for detecting antidepressant drug effects. Chicks were returned to their home cage following tests. These procedures were approved by the University of Mississippi's IACUC (Protocol #12-021).

Statistical Analysis and Results. Data were screened for outliers before data analyses. This included chicks that were low weight, failed to display a stress response upon isolation and/or did not enter into behavioral despair.

Figure 17A:
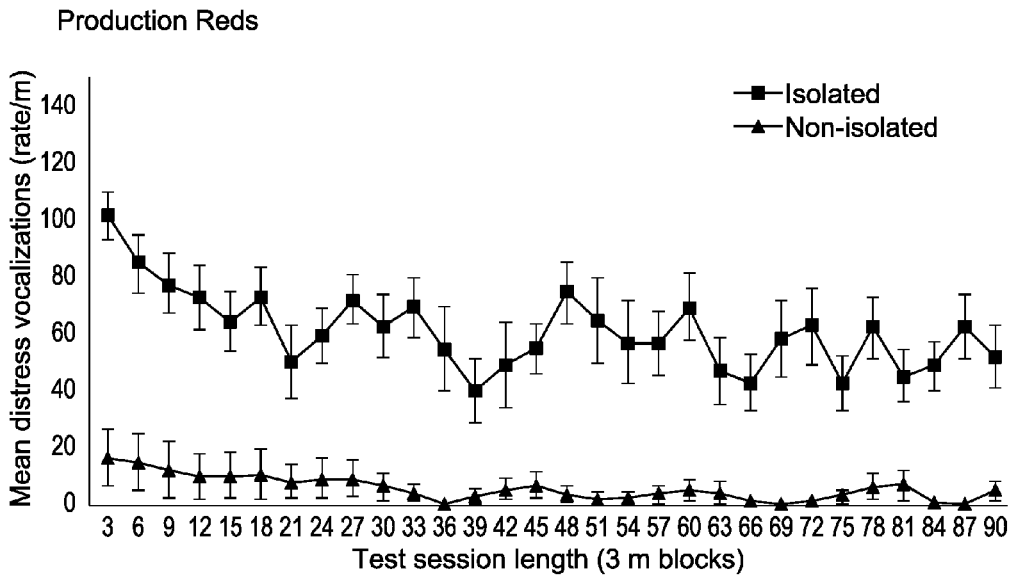
FIG. 17A and FIG. 17B show the effects of isolation and non-isolation (social) conditions on mean distress vocalizations across a 90-minute test period for Production Red strain chicks (FIG. 17A) and Black Australorp strain chicks (FIG. 17B). Triangle symbols represent non-isolated (social) test condition and square symbols represent isolated test condition. Values represent mean (±SEM) DVoc for each 3 min time block. Sample sizes were n=9-12.

Results highlighting the isolation stress effect and behavioral despair in Production Reds are summarized in FIG. 17A. A 2-way ANOVA revealed a significant main effect for Isolation treatment, $F(1,19)=50.06$, $p<00001$, a significant main effect for Session length $F(29,551)=3.82$, $p<0.0001$ and a significant Isolation×Session interaction term, $F(29,551)=1.66$, $p=0.018$. Simple effect analyses revealed a significant effect of Session length in the Isolated group, $F(1,232)=2.75$, $p<0.0001$) but not in the non-isolated group (p=n.s.). This pattern in DVoc rates illustrates the two phases of the Anxiety-Depression model.

Figure 17B:
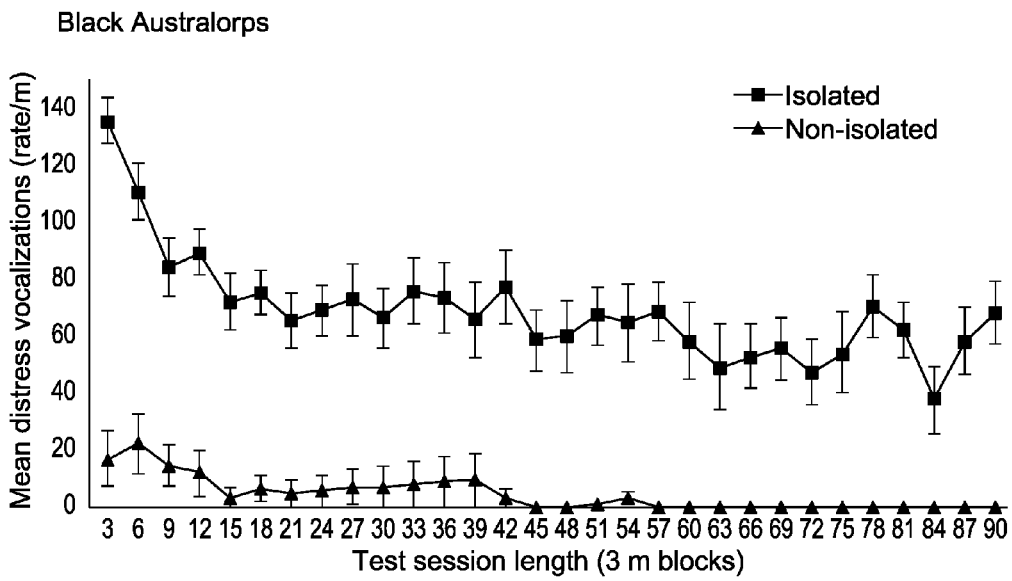

Results highlighting the isolation stress effect and behavioral despair in Black Australorps are summarized in FIG. 17B. A 2-way ANOVA revealed a significant main effect for Isolation treatment, $F(1,21)=65.11$, $p<00001$ and a significant main effect for Session length $F(29,609)=3.84$, $p<0.0001$. Interestingly, the Isolation×Session interaction term failed to reach statistical significance (p=0.15). It should be noted that DVoc data from non-isolated chicks reflects the sum of 3 chicks in the test apparatus and I make no adjustment in rates for this treatment condition; nevertheless, DVoc rates remained relatively low throughout the test session. A 1-way repeated measures ANOVA on isolated chicks revealed a significant effect of Session length, $F(1,290)=2.64$, $p<0.0001$). As before, this pattern in DVoc rates illustrates the two phases of the Anxiety-Depression model.

Behavioral despair onset was measured from pooled data from the vehicle-isolated groups in the dose response studies. Five cohorts (hatches) of each strain were used for dose response studies (one dose response/drug probe except two for ketamine). Separate 1-way ANOVAs on DVoc rates in each phase (Anxiety-like phase: 0-5 min, Depression-like phase 30-90 min) of the model were conducted within each strain to determine hatch differences in base rates in vocalizations. These analyses revealed that 1 cohort in each strain, while showing patterns of behavioral despair, displayed significantly different base rate DVoc rates from their respective cohorts. These cohorts were removed before calculating behavioral despair onset thresholds. For this measure, I determined the time point at which each chick's DVoc rate/min from its anxiety-like phase (first 3 min block) declined by 25, 50, 75 and 95% to the rate/min during its depression-like phase (30-90 min). From these data, ANOVA revealed a significant main effect for Strain $F(1,84)=6.59$, $p<0.05$ and a significant main effect for behavioral despair onset threshold, $F(3,252)=77.15$, $p<0.0001$. The Strain×Threshold interaction term was not statistically significant. The results are summarized in FIG. 18.

To determine whether drug probes possessed antidepressant effects, DVoc rates/min for depression-like phase (30-90 min test period) were analyzed via 1-way ANOVAs followed by Fisher's LSD post hoc tests. A drug dose that produced a statistically significant increase in DVoc rate ($p<0.05$) compared to vehicle-treated chicks was considered to possess antidepressant effects (i.e., attenuated behavioral despair in the model). The results for drug probes imipramine, fluoxetine, maprotiline, and ketamine in Black Australorps and Production Reds are summarized in FIGS. 19A, B, C, and D, respectively.

While the foregoing description has set forth the various embodiments of the present invention in particular detail, it must be understood that numerous modifications, substitutions and changes can be undertaken without departing from the true spirit and scope of the present invention as defined by the ensuing claims. The invention is therefore not limited to specific preferred embodiments as described, but is only limited as defined by the following claims.

I claim:

1. A method to screen for treatment-resistant antidepressant drugs, wherein at least one drug is screened for antidepressant activity in a plurality of fowl chicks with stress vulnerability comprising:
  a) providing said plurality of fowl chicks with stress vulnerability, wherein a first portion of said plurality of fowl chicks with stress vulnerability receives said at least one drug and a second portion of said plurality of fowl chicks with stress vulnerability do not receive said at least one drug, and wherein said plurality of fowl chicks with stress vulnerability is insensitive to at least two classes of antidepressants selected from tricyclic antidepressants, selective norepinephrine reuptake inhibitors (SNRI), and selective serotonin reuptake inhibitors (SSRI), and wherein said plurality of fowl chicks with stress vulnerability is sensitive to the N-Methyl-D-aspartate (NMDA) receptor antagonist ketamine;

b) audibly separating at least one fowl chick with stress vulnerability individually from said first portion and second portion of fowl chicks with stress vulnerability without noxious stimulus;

c) recording distress vocalizations of said at least one individually separated fowl chick with stress vulnerability at a recording time period;

d) converting distress vocalizations of said at least one individually separated fowl chick with stress vulnerability over time into a DVocs rate; and e) determining the effectiveness of said at least one drug by evaluating the DVocs rate of said at least one individually separated fowl chick with stress vulnerability from said first portion of fowl chicks with stress vulnerability and from said second portion of fowl chicks with stress vulnerability at said recording time period;

wherein said plurality of fowl chicks with stress vulnerability comprises Black Australorps.

2. The method of claim 1, wherein said at least one fowl chick with stress vulnerability is individually separated from said first portion and second portion of fowl chicks with stress vulnerability for between 20 to 120 minutes.

3. The method of claim 2, wherein said at least one fowl chick with stress vulnerability is individually separated from said first portion and second portion of fowl chicks with stress vulnerability for between 30 to 90 minutes.

4. The method of claim 2, wherein said DVocs rate is indicative of depression in said at least one fowl chick with stress vulnerability.

5. The method of claim 4, wherein said at least one drug has antidepressant activity as shown by an increase in said DVocs rate.

6. The method of claim 1, further comprising adjusting said at least one drug to determine optimum dosage.

* * * * *

UNITED STATES PATENT AND TRADEMARK OFFICE
CERTIFICATE OF CORRECTION

PATENT NO. : 8,999,293 B2  Page 1 of 1
APPLICATION NO. : 13/895107
DATED : April 7, 2015
INVENTOR(S) : Kenneth J. Sufka It is certified that error appears in the above-identified patent and that said Letters Patent is hereby corrected as shown below:

On the title page item (60), in the Related U.S. Application Data, Provisional Application No. should read -60/726,121-.

Signed and Sealed this
Twenty-second Day of March, 2016

Michelle K. Lee
*Director of the United States Patent and Trademark Office*